(12) United States Patent
Wolf et al.

(10) Patent No.: US 9,226,742 B2
(45) Date of Patent: Jan. 5, 2016

(54) RESTRICTED WEDGE SUTURE ANCHOR AND METHOD FOR SOFT TISSUE REPAIR

(75) Inventors: Steven Wolf, Mission Viejo, CA (US); Emil Karapetian, Huntington Beach, CA (US); George W. White, Corona, CA (US); David Gregoire, Mission Viejo, CA (US)

(73) Assignee: ArthroCare Corporation, Austin, TX (US)

( * ) Notice: Subject to any disclaimer, the term of this patent is extended or adjusted under 35 U.S.C. 154(b) by 365 days.

(21) Appl. No.: 13/359,673

(22) Filed: Jan. 27, 2012

(65) Prior Publication Data

US 2013/0197577 A1    Aug. 1, 2013

(51) Int. Cl.
*A61B 17/04*    (2006.01)

(52) U.S. Cl.
CPC ....... *A61B 17/0401* (2013.01); *A61B 2017/043* (2013.01); *A61B 2017/0409* (2013.01); *A61B 2017/0412* (2013.01); *A61B 2017/0451* (2013.01)

(58) Field of Classification Search
CPC .................. A61B 17/0401; A61B 2017/0404; A61B 2017/0406; A61B 2017/0408; A61B 2017/0409; A61B 2017/0411; A61B 2017/0412; A61B 2017/0414; A61B 2017/0416
USPC .................................................. 606/232, 215
See application file for complete search history.

(56) References Cited

U.S. PATENT DOCUMENTS

| 918,570 | A | 4/1909 | Mather | 292/318 |
|---|---|---|---|---|
| 1,153,053 | A | 9/1915 | Forster | 43/44.85 |
| 1,565,041 | A | 12/1925 | Arneu | 24/129 R |
| 2,269,963 | A | 1/1942 | Wrapler | 604/604 |
| 2,485,531 | A | 10/1949 | Dzus et al. | 128/92 |
| 2,600,395 | A | 6/1952 | Domoj et al. | 87/13 |
| 3,143,916 | A | 8/1964 | Rice | 85/71 |
| 3,942,407 | A | 3/1976 | Mortensen | 85/71 |
| 3,946,740 | A | 3/1976 | Bassett | 128/334 |
| 3,994,521 | A | 11/1976 | Van Gompel | 292/319 |
| 4,109,658 | A | 8/1978 | Hughes | 128/340 |
| 4,210,148 | A | 7/1980 | Stivala | 606/232 |
| 4,274,324 | A | 6/1981 | Giannuzzi | 411/38 |
| 4,301,551 | A | 11/1981 | Dore et al. | 623/13.3 |

(Continued)

FOREIGN PATENT DOCUMENTS

| DE | 3509417 | 9/1986 | ............. A61B 17/58 |
|---|---|---|---|
| EP | 0 535 906 A2 | 4/1993 | ............. A61B 17/04 |

(Continued)

OTHER PUBLICATIONS

PCT Search Report and Written Opinion for PCT/US06/20657 7pgs, Mailed Oct. 2, 2007.

(Continued)

*Primary Examiner* — Tuan V Nguyen
(74) *Attorney, Agent, or Firm* — Norman F. Hainer, Jr.

(57) ABSTRACT

A suture anchor device and method for attaching soft tissue to bone includes an anchor body and a suture locking wedge movably disposed within the anchor body. Tension applied to one side of a suture causes the suture locking wedge to move in a translational and angular dimension to a position which compresses the suture, thereby locking the suture in the anchor. The anchor body includes tracks or slots which guide the suture locking wedge from the unlocked open configuration to the locked configuration.

34 Claims, 12 Drawing Sheets

(56) References Cited

U.S. PATENT DOCUMENTS

| | | | |
|---|---|---|---|
| 4,319,428 A | 3/1982 | Fox | 47/42 |
| 4,345,601 A | 8/1982 | Fukuda | 128/339 |
| 4,373,530 A | 2/1983 | Kilejian | 128/334 R |
| 4,384,389 A | 5/1983 | Sato | 24/136 K |
| 4,409,974 A | 10/1983 | Freedland | 128/92 |
| 4,456,270 A | 6/1984 | Zettl et al. | 279/62 |
| 4,467,478 A | 8/1984 | Jurgutis | 606/75 |
| 4,483,023 A | 11/1984 | Hoffman, Jr. et al. | 623/13.15 |
| 4,493,323 A | 1/1985 | Albright et al. | 128/340 |
| 4,580,936 A | 4/1986 | Francis et al. | 411/38 |
| 4,590,928 A | 5/1986 | Hunt et al. | 606/72 |
| 4,597,776 A | 7/1986 | Ullman et al. | 48/197 R |
| 4,605,414 A | 8/1986 | Czajka | 623/13.11 |
| 4,621,640 A | 11/1986 | Mulhollan et al. | 128/340 |
| 4,635,637 A | 1/1987 | Schreiber | 128/337 |
| 4,657,461 A | 4/1987 | Smith | 411/340 |
| 4,672,957 A | 6/1987 | Hourahane | 606/80 |
| 4,680,835 A | 7/1987 | Horng | 24/712.5 |
| 4,712,542 A | 12/1987 | Daniel et al. | 606/96 |
| 4,721,103 A | 1/1988 | Freedland | 128/92 |
| 4,731,084 A | 3/1988 | Dunn et al. | 623/13.19 |
| 4,738,255 A | 4/1988 | Goble et al. | 128/92 YF |
| 4,741,330 A | 5/1988 | Hayhurst | 123/43 R |
| 4,750,492 A | 6/1988 | Jacobs | 606/230 |
| 4,772,286 A | 9/1988 | Goble et al. | 623/13.14 |
| 4,779,616 A | 10/1988 | Johnson et al. | 606/148 |
| 4,809,408 A | 3/1989 | Abrahamson | 24/136 K |
| 4,823,780 A | 4/1989 | Odensten et al. | 606/96 |
| 4,828,439 A | 5/1989 | Giannuzzi | 411/37 |
| 4,851,005 A | 7/1989 | Hunt et al. | 623/18 |
| 4,870,957 A | 10/1989 | Goble et al. | 606/73 |
| 4,917,700 A | 4/1990 | Aikins | 623/13.19 |
| 4,926,860 A | 5/1990 | Stice et al. | 606/144 |
| 4,935,027 A | 6/1990 | Yoon | 606/146 |
| 4,946,467 A | 8/1990 | Ohi et al. | 606/228 |
| 4,946,468 A | 8/1990 | Li | 606/232 |
| 4,957,498 A | 9/1990 | Caspari et al. | 606/146 |
| 4,968,315 A | 11/1990 | Gatturna | 606/72 |
| 4,981,149 A | 1/1991 | Yoon et al. | 128/898 |
| 4,987,665 A | 1/1991 | Dumican et al. | 28/218 |
| 5,002,550 A | 3/1991 | Li | 606/139 |
| 5,019,093 A | 5/1991 | Kaplan et al. | 606/228 |
| 5,037,422 A | 8/1991 | Hayhurst | 606/72 |
| 5,046,513 A | 9/1991 | Gatturna | 128/898 |
| 5,059,201 A | 10/1991 | Asnis | 606/144 |
| 5,062,344 A | 11/1991 | Gerker | 87/8 |
| 5,085,661 A | 2/1992 | Moss | 606/139 |
| 5,147,166 A | 9/1992 | Harker | 411/29 |
| 5,195,542 A | 3/1993 | Gazielly et al. | 60/244 |
| 5,203,787 A | 4/1993 | Noblitt et al. | 606/232 |
| RE34,293 E | 6/1993 | Goble et al. | 623/13.14 |
| 5,217,495 A | 6/1993 | Kaplan et al. | 623/13.18 |
| 5,219,359 A | 6/1993 | McQuilkin et al. | 606/232 |
| 5,224,946 A | 7/1993 | Hayhurst | 606/232 |
| 5,258,016 A | 11/1993 | DiPoto et al. | 606/232 |
| 5,263,984 A | 11/1993 | Li | 623/13.18 |
| 5,275,176 A | 1/1994 | Chandler | 606/242 |
| 5,304,184 A | 4/1994 | Hathaway et al. | 606/144 |
| 5,306,290 A | 4/1994 | Martins et al. | 606/232 |
| 5,324,308 A | 6/1994 | Pierce | 606/232 |
| 5,326,205 A | 7/1994 | Anspach, III et al. | 411/43 |
| 5,330,442 A | 7/1994 | Green | 606/232 |
| 5,330,468 A | 7/1994 | Burkhart | 606/96 |
| 5,330,488 A | 7/1994 | Goldrath | 606/148 |
| 5,336,240 A | 8/1994 | Metzler | 606/232 |
| 5,354,298 A | 10/1994 | Lee et al. | 606/72 |
| 5,364,407 A | 11/1994 | Poll | 606/139 |
| 5,376,118 A | 12/1994 | Kaplan et al. | 623/23.72 |
| 5,383,905 A | 1/1995 | Gold et al. | 606/232 |
| 5,405,352 A | 4/1995 | Weston | 606/148 |
| 5,405,359 A | 4/1995 | Pierce | 606/232 |
| 5,411,523 A | 5/1995 | Goble | 606/232 |
| 5,413,579 A | 5/1995 | Tom Du | 606/87 |
| 5,417,691 A | 5/1995 | Hayhurst | 606/72 |
| 5,417,699 A | 5/1995 | Klein et al. | 606/139 |
| 5,417,712 A | 5/1995 | Whitaker et al. | 606/232 |
| 5,431,666 A | 7/1995 | Sauer et al. | 606/139 |
| 5,441,508 A | 8/1995 | Gazielly et al. | 606/151 |
| 5,445,167 A | 8/1995 | Yoon et al. | 128/898 |
| 5,450,860 A | 9/1995 | O'Connor | 606/224 |
| 5,454,823 A | 10/1995 | Richardson et al. | 606/148 |
| 5,464,427 A | 11/1995 | Curtis et al. | 606/232 |
| 5,470,335 A | 11/1995 | DuToit | 606/73 |
| 5,472,452 A | 12/1995 | Trott | 606/232 |
| 5,480,403 A | 1/1996 | Lee et al. | 606/72 |
| 5,486,197 A | 1/1996 | Le et al. | 606/232 |
| 5,499,991 A | 3/1996 | Garman et al. | 606/148 |
| 5,501,683 A | 3/1996 | Trott | 606/72 |
| 5,501,695 A | 3/1996 | Anspach, Jr. et al. | 606/72 |
| 5,505,735 A | 4/1996 | Li | 606/72 |
| 5,514,159 A | 5/1996 | Matula et al. | 606/232 |
| 5,520,700 A | 5/1996 | Beyar et al. | 606/139 |
| 5,522,820 A | 6/1996 | Caspari et al. | 606/148 |
| 5,527,322 A | 6/1996 | Klein et al. | 606/144 |
| 5,527,343 A | 6/1996 | Bonutti | 606/232 |
| 5,531,763 A | 7/1996 | Mastri et al. | 606/148 |
| 5,531,792 A | 7/1996 | Huene | 623/16 |
| 5,534,012 A | 7/1996 | Bonutti | 606/232 |
| 5,540,703 A | 7/1996 | Barker, Jr. et al. | 606/139 |
| 5,545,180 A | 8/1996 | Le et al. | 606/232 |
| 5,549,617 A | 8/1996 | Green et al. | 606/144 |
| 5,549,630 A | 8/1996 | Bonutti | 606/232 |
| 5,553,360 A | 9/1996 | Lucas et al. | 24/136 K |
| 5,562,689 A | 10/1996 | Green et al. | 606/151 |
| 5,569,305 A | 10/1996 | Bonutti | 606/232 |
| 5,569,306 A | 10/1996 | Thal | 606/232 |
| 5,571,104 A | 11/1996 | Li | 606/72 |
| 5,571,120 A | 11/1996 | Yoon | 606/148 |
| 5,573,540 A | 11/1996 | Yoon | 606/139 |
| 5,573,542 A | 11/1996 | Stevens | 606/144 |
| 5,573,548 A | 11/1996 | Nazre et al. | 606/232 |
| 5,575,801 A | 11/1996 | Habermeyer et al. | 606/148 |
| 5,584,835 A | 12/1996 | Greenfield | 606/73 |
| 5,584,839 A | 12/1996 | Gieringer | 606/96 |
| 5,584,860 A | 12/1996 | Goble et al. | 606/232 |
| 5,584,862 A | 12/1996 | Bonutti | 606/232 |
| 5,591,207 A | 1/1997 | Coleman | 606/232 |
| 5,593,189 A | 1/1997 | Little | 289/17 |
| 5,601,558 A | 2/1997 | Torrie et al. | 606/72 |
| 5,609,597 A | 3/1997 | Lehrer | 606/139 |
| 5,611,801 A | 3/1997 | Songer | 606/73 |
| 5,613,974 A | 3/1997 | Andreas et al. | 606/144 |
| 5,618,290 A | 4/1997 | Toy et al. | 606/139 |
| 5,618,314 A | 4/1997 | Harwin et al. | 606/232 |
| 5,626,614 A | 5/1997 | Hart | 606/232 |
| 5,630,824 A | 5/1997 | Hart | 606/139 |
| 5,632,748 A | 5/1997 | Beck, Jr. et al. | 606/72 |
| 5,645,589 A | 7/1997 | Li | 623/16 |
| 5,647,874 A | 7/1997 | Hayhurst | 606/72 |
| 5,649,940 A | 7/1997 | Hart et al. | 606/148 |
| 5,649,963 A | 7/1997 | McDevitt | 606/232 |
| 5,658,313 A | 8/1997 | Thal | 606/232 |
| 5,665,110 A | 9/1997 | Chervitz et al. | 606/232 |
| 5,665,112 A | 9/1997 | Thal | 606/232 |
| 5,667,528 A | 9/1997 | Colligan | 606/224 |
| D385,352 S | 10/1997 | Bales et al. | D24/145 |
| 5,681,333 A | 10/1997 | Burkhart et al. | 606/148 |
| 5,681,351 A | 10/1997 | Jamiolkowski et al. | 606/232 |
| 5,683,418 A | 11/1997 | Luscombe et al. | 606/232 |
| 5,683,419 A | 11/1997 | Thal | 606/232 |
| 5,690,649 A | 11/1997 | Li | 606/139 |
| 5,693,060 A | 12/1997 | Martin | 606/148 |
| 5,697,950 A | 12/1997 | Fucci et al. | 606/232 |
| 5,702,397 A | 12/1997 | Goble et al. | 606/72 |
| 5,702,398 A | 12/1997 | Tarabishy | |
| 5,707,362 A | 1/1998 | Yoon | 604/164 |
| 5,707,394 A | 1/1998 | Miller et al. | 606/232 |
| 5,709,708 A | 1/1998 | Thal | 606/232 |
| 5,720,765 A | 2/1998 | Thal | 606/232 |
| 5,725,529 A | 3/1998 | Nicholson et al. | 606/72 |
| 5,725,541 A | 3/1998 | Anspach, III et al. | 606/151 |
| 5,728,136 A | 3/1998 | Thal | 606/232 |
| 5,733,307 A | 3/1998 | Dinsdale | 606/232 |
| 5,741,281 A | 4/1998 | Martin | 606/148 |

(56) References Cited

U.S. PATENT DOCUMENTS

| | | | |
|---|---|---|---|
| 5,741,282 A | 4/1998 | Anspach, III et al. | 606/151 |
| 5,766,250 A | 6/1998 | Chervitz et al. | 623/13 |
| 5,782,863 A | 7/1998 | Bartlett | 606/232 |
| 5,782,864 A | 7/1998 | Lizardi | 606/232 |
| 5,782,865 A | 7/1998 | Grotz | 606/72 |
| 5,791,899 A | 8/1998 | Sachdeva | 433/173 |
| 5,792,152 A | 8/1998 | Klein et al. | 606/144 |
| 5,797,927 A | 8/1998 | Yoon | 606/144 |
| 5,797,963 A | 8/1998 | McDevitt | 606/232 |
| 5,810,848 A | 9/1998 | Hayhurst | 606/144 |
| 5,810,854 A | 9/1998 | Beach | 606/232 |
| 5,814,052 A | 9/1998 | Nakao et al. | 606/148 |
| 5,814,071 A | 9/1998 | McDevitt et al. | 606/232 |
| 5,814,072 A | 9/1998 | Bonutti | 606/232 |
| 5,843,111 A | 12/1998 | Vijfvinkel | 606/171 |
| 5,849,004 A | 12/1998 | Bramlet | 606/232 |
| 5,860,978 A | 1/1999 | McDevitt | 606/72 |
| 5,860,991 A | 1/1999 | Klein et al. | 606/144 |
| 5,860,992 A | 1/1999 | Daniel et al. | 606/145 |
| 5,868,789 A | 2/1999 | Huebner | 606/232 |
| 5,879,372 A | 3/1999 | Bartlett | 606/232 |
| 5,882,340 A | 3/1999 | Yoon | 604/164 |
| 5,885,294 A | 3/1999 | Pedlick et al. | 606/80 |
| 5,891,168 A | 4/1999 | Thal | 606/232 |
| 5,893,850 A | 4/1999 | Cachia | 606/72 |
| 5,902,311 A | 5/1999 | Andreas et al. | 606/144 |
| 5,904,692 A | 5/1999 | Steckel et al. | 606/139 |
| 5,911,721 A | 6/1999 | Nicholson et al. | 606/72 |
| 5,921,994 A | 7/1999 | Andreas et al. | 606/144 |
| 5,935,107 A | 8/1999 | Taylor et al. | 604/164 |
| 5,935,129 A | 8/1999 | Mdevitt | 606/72 |
| 5,941,900 A | 8/1999 | Bonutti | 606/232 |
| 5,941,901 A | 8/1999 | Egan | 606/232 |
| 5,944,724 A | 8/1999 | Lizardi | 606/104 |
| 5,944,739 A | 8/1999 | Zlock et al. | 606/232 |
| 5,947,982 A | 9/1999 | Duran | 606/139 |
| 5,948,000 A | 9/1999 | Larsen et al. | 606/232 |
| 5,948,001 A | 9/1999 | Larsen | 606/232 |
| 5,948,002 A | 9/1999 | Bonutti | 606/232 |
| 5,957,953 A | 9/1999 | DiPoto et al. | 606/232 |
| 5,957,968 A | 9/1999 | Belden et al. | 607/126 |
| 5,961,530 A | 10/1999 | Moore et al. | 606/148 |
| 5,961,538 A | 10/1999 | Pedlick et al. | 606/232 |
| 5,968,044 A | 10/1999 | Nicholson et al. | 606/72 |
| 5,980,558 A | 11/1999 | Wiley | 606/232 |
| 5,980,559 A | 11/1999 | Bonutti | 606/232 |
| 5,984,933 A | 11/1999 | Yoon | 606/148 |
| 5,993,459 A | 11/1999 | Larsen | 606/104 |
| 6,001,104 A | 12/1999 | Benderev et al. | 606/80 |
| 6,001,109 A | 12/1999 | Kontos | 606/148 |
| 6,007,566 A | 12/1999 | Wenstrom | 606/232 |
| 6,007,567 A | 12/1999 | Bonutti | 606/232 |
| 6,010,525 A | 1/2000 | Bonutti et al. | 606/232 |
| 6,013,083 A | 1/2000 | Bennett | 606/104 |
| 6,017,346 A | 1/2000 | Grotz | 606/72 |
| 6,022,360 A | 2/2000 | Reimels et al. | 606/144 |
| 6,022,373 A | 2/2000 | Li | 606/232 |
| 6,024,758 A | 2/2000 | Thal | 606/232 |
| 6,033,430 A | 3/2000 | Bonutti | 606/232 |
| 6,036,699 A | 3/2000 | Andreas et al. | 606/139 |
| 6,045,571 A | 4/2000 | Hill et al. | 606/228 |
| 6,045,572 A | 4/2000 | Johnson et al. | 606/232 |
| 6,045,573 A | 4/2000 | Wenstrom et al. | 606/232 |
| 6,045,574 A | 4/2000 | Thal | 606/232 |
| 6,048,351 A | 4/2000 | Gordon et al. | 606/144 |
| 6,051,006 A | 4/2000 | Shluzas et al. | 606/148 |
| 6,053,935 A | 4/2000 | Brenneman et al. | 606/232 |
| 6,056,773 A | 5/2000 | Bonutti | 606/232 |
| 6,066,146 A | 5/2000 | Carroll et al. | 606/148 |
| 6,066,160 A * | 5/2000 | Colvin et al. | 606/232 |
| 6,068,648 A | 5/2000 | Cole et al. | 606/232 |
| 6,086,608 A | 7/2000 | Ek et al. | 606/232 |
| 6,096,051 A | 8/2000 | Kortenbach et al. | 606/144 |
| 6,102,934 A | 8/2000 | Li | 606/232 |
| 6,117,160 A | 9/2000 | Bonutti | 606/215 |
| 6,117,161 A | 9/2000 | Li | 606/232 |
| 6,143,004 A | 11/2000 | Davis et al. | 606/144 |
| 6,146,386 A | 11/2000 | Blackman | 606/103 |
| 6,146,406 A | 11/2000 | Shluzas et al. | 606/232 |
| 6,149,669 A | 11/2000 | Li | 606/232 |
| 6,156,039 A | 12/2000 | Thai | 606/72 |
| 6,156,056 A | 12/2000 | Kearns et al. | 606/232 |
| 6,159,235 A | 12/2000 | Kim | 606/232 |
| 6,162,537 A | 12/2000 | Martin et al. | 428/373 |
| 6,171,317 B1 | 1/2001 | Jackson et al. | 606/148 |
| 6,200,329 B1 | 3/2001 | Fung et al. | 606/232 |
| 6,200,893 B1 | 3/2001 | Sneh | 438/685 |
| 6,206,895 B1 | 3/2001 | Levinson | 606/144 |
| 6,217,592 B1 | 4/2001 | Freda et al. | 606/145 |
| 6,221,107 B1 | 4/2001 | Steiner et al. | 623/13.14 |
| 6,228,096 B1 | 5/2001 | Marchand | 606/139 |
| 6,241,736 B1 | 6/2001 | Sater | 606/104 |
| 6,267,766 B1 | 7/2001 | Burkhart | 606/72 |
| 6,280,474 B1 | 8/2001 | Cassidy et al. | 623/16.11 |
| 6,293,961 B2 | 9/2001 | Schwartz | 606/232 |
| 6,295,700 B1 | 10/2001 | Plzak | 24/134 R |
| 6,315,781 B1 | 11/2001 | Reinhardt | 606/108 |
| 6,319,252 B1 | 11/2001 | McDevitt et al. | 606/60 |
| 6,319,269 B1 | 11/2001 | Li | 606/232 |
| 6,319,271 B1 | 11/2001 | Schwartz | 606/232 |
| 6,328,758 B1 | 12/2001 | Tornier et al. | 606/232 |
| 6,355,053 B1 | 3/2002 | Li | 606/232 |
| 6,409,743 B1 | 6/2002 | Fenton | 606/232 |
| 6,432,123 B2 | 8/2002 | Schwartz et al. | 606/232 |
| 6,436,109 B1 | 8/2002 | Kontes | 606/148 |
| 6,451,030 B2 | 9/2002 | Li et al. | 606/139 |
| 6,464,713 B2 | 10/2002 | Bonutti | 606/232 |
| 6,468,293 B2 | 10/2002 | Bonutti et al. | 606/232 |
| 6,471,715 B1 | 10/2002 | Weiss | 606/216 |
| 6,475,230 B1 | 11/2002 | Bonutti et al. | 606/232 |
| 6,491,714 B1 | 12/2002 | Bennett | 606/232 |
| 6,517,542 B1 | 2/2003 | Papay et al. | 606/73 |
| 6,520,980 B1 | 2/2003 | Foerster | 606/232 |
| 6,524,317 B1 | 2/2003 | Ritchart et al. | 606/72 |
| 6,527,794 B1 | 3/2003 | McDevitt et al. | 606/232 |
| 6,540,770 B1 | 4/2003 | Tornier et al. | 606/232 |
| 6,569,187 B1 | 5/2003 | Bonutti et al. | 606/232 |
| 6,575,987 B2 | 6/2003 | Gellman et al. | 606/151 |
| 6,582,453 B1 | 6/2003 | Tran et al. | 606/232 |
| 6,585,730 B1 | 7/2003 | Foerster | 606/232 |
| 6,635,073 B2 | 10/2003 | Bonutti | 606/232 |
| 6,638,279 B2 | 10/2003 | Bonutti | 606/60 |
| 6,645,227 B2 | 11/2003 | Fallin et al. | 606/232 |
| 6,648,903 B1 | 11/2003 | Pierson, III | 606/232 |
| 6,652,561 B1 | 11/2003 | Tran | 606/232 |
| 6,656,183 B2 | 12/2003 | Colleran et al. | 606/232 |
| 6,660,008 B1 | 12/2003 | Foerster et al. | 606/72 |
| 6,660,023 B2 | 12/2003 | McDevitt et al. | 606/232 |
| 6,673,094 B1 | 1/2004 | McDevitt et al. | 606/232 |
| 6,679,896 B2 | 1/2004 | Gellman et al. | 606/148 |
| 6,682,549 B2 | 1/2004 | Bartlett | 606/232 |
| 6,689,154 B2 | 2/2004 | Bartlett | 606/232 |
| 6,692,516 B2 | 2/2004 | West et al. | 606/232 |
| 6,736,829 B1 | 5/2004 | Li et al. | 606/232 |
| 6,770,076 B2 | 8/2004 | Foerster | 606/72 |
| 6,780,198 B1 | 8/2004 | Gregoire et al. | 606/232 |
| 6,855,157 B2 | 2/2005 | Foerster et al. | 606/232 |
| 6,860,887 B1 | 3/2005 | Frankie | 606/104 |
| 6,887,259 B2 | 5/2005 | Lizardi | 606/232 |
| 6,939,379 B2 | 9/2005 | Sklar | 623/13.14 |
| 6,972,027 B2 | 12/2005 | Fallin et al. | 606/232 |
| 7,083,638 B2 | 8/2006 | Foerster | 606/232 |
| 7,087,064 B1 | 8/2006 | Hyde | 606/142 |
| 7,090,690 B2 | 8/2006 | Foerster et al. | 606/232 |
| 7,104,999 B2 | 9/2006 | Overaker | 606/142 |
| 7,144,415 B2 | 12/2006 | Del Rio et al. | 606/232 |
| 7,150,750 B2 | 12/2006 | Damarati | 623/17.11 |
| 7,150,757 B2 | 12/2006 | Fallin et al. | 606/232 |
| 7,247,164 B1 | 7/2007 | Ritchart et al. | 606/232 |
| 7,320,701 B2 | 1/2008 | Haut et al. | 606/232 |
| 7,329,272 B2 | 2/2008 | Burkhart et al. | 606/232 |
| 7,381,213 B2 | 6/2008 | Lizardi | 606/232 |
| 7,410,489 B2 | 8/2008 | Dakin et al. | 606/103 |
| 7,556,640 B2 | 7/2009 | Foerster | 606/232 |

(56) References Cited

U.S. PATENT DOCUMENTS

| | | | |
|---|---|---|---|
| 7,588,587 B2 | 9/2009 | Barbieri et al. | 606/232 |
| 7,615,061 B2 | 11/2009 | White et al. | 606/148 |
| 7,637,926 B2 | 12/2009 | Foerster et al. | 606/232 |
| 7,674,274 B2 | 3/2010 | Foerster et al. | 606/232 |
| 7,682,374 B2 | 3/2010 | Foerster | 606/72 |
| 7,695,494 B2 | 4/2010 | Foerster | 606/232 |
| 7,837,710 B2 | 11/2010 | Lombardo et al. | 606/232 |
| 7,867,251 B2 | 1/2011 | Colleran et al. | 606/232 |
| 7,938,847 B2 | 5/2011 | Fanton et al. | 606/232 |
| 7,963,972 B2 | 6/2011 | Foerster et al. | 606/139 |
| 7,981,140 B2 | 7/2011 | Burkhart | 606/232 |
| 8,109,966 B2 | 2/2012 | Ritchart et al. | 606/232 |
| 8,133,258 B2 | 3/2012 | Foerster et al. | 606/232 |
| 8,137,381 B2 | 3/2012 | Foerster et al. | 606/232 |
| 8,317,829 B2 | 11/2012 | Foerster et al. | 606/232 |
| 8,425,536 B2 | 4/2013 | Foerster et al. | 606/232 |
| 8,444,672 B2 | 5/2013 | Foerster | 606/232 |
| 8,685,060 B2 | 4/2014 | Foerster | 606/232 |
| 2003/0105489 A1 | 6/2003 | Eichhorn et al. | 606/232 |
| 2003/0167062 A1 | 9/2003 | Gambale | 606/232 |
| 2003/0195563 A1 | 10/2003 | Foerster | 606/232 |
| 2003/0195564 A1 | 10/2003 | Tran et al. | 606/232 |
| 2004/0133239 A1 | 7/2004 | Singhatat | 606/232 |
| 2004/0138683 A1 | 7/2004 | Shelton et al. | 606/151 |
| 2004/0138706 A1 | 7/2004 | Abrams et al. | 606/232 |
| 2004/0153074 A1 | 8/2004 | Bojarski et al. | 606/232 |
| 2004/0236336 A1 | 11/2004 | Foerster et al. | 606/72 |
| 2005/0033364 A1 | 2/2005 | Gregoire et al. | 606/232 |
| 2005/0080455 A1 | 4/2005 | Schmieding et al. | 606/232 |
| 2005/0090827 A1 | 4/2005 | Gedebou | 606/72 |
| 2005/0273101 A1 | 12/2005 | Schumacher | 606/72 |
| 2005/0277986 A1 | 12/2005 | Foerster | 606/232 |
| 2006/0004364 A1 | 1/2006 | Green et al. | 606/72 |
| 2006/0074422 A1 | 4/2006 | Story et al. | 606/142 |
| 2006/0079904 A1 | 4/2006 | Thal | 606/72 |
| 2006/0106423 A1 | 5/2006 | Weisel et al. | 606/232 |
| 2006/0161159 A1 | 7/2006 | Dreyfuss et al. | 606/72 |
| 2006/0271060 A1 | 11/2006 | Gordon | 606/232 |
| 2006/0271105 A1 | 11/2006 | Foerster | 606/232 |
| 2006/0282081 A1 | 12/2006 | Fanton et al. | 606/232 |
| 2007/0142838 A1 | 6/2007 | Jordan | 606/75 |
| 2007/0156148 A1 | 7/2007 | Fanton et al. | 606/72 |
| 2007/0276437 A1 * | 11/2007 | Call et al. | 606/232 |
| 2008/0051836 A1 | 2/2008 | Foerster et al. | 606/232 |
| 2008/0119849 A1 | 5/2008 | Beardsley et al. | 606/232 |
| 2008/0319478 A1 | 12/2008 | Foerster et al. | 606/148 |
| 2009/0069823 A1 | 3/2009 | Foerster et al. | 606/103 |
| 2009/0222040 A1 | 9/2009 | Foerster et al. | 606/232 |
| 2009/0222041 A1 | 9/2009 | Foerster et al. | 606/232 |
| 2009/0248068 A1 | 10/2009 | Lombardo et al. | 606/232 |
| 2010/0191283 A1 | 7/2010 | Foerster et al. | 606/232 |
| 2013/0060280 A1 | 3/2013 | Wolf et al. | 606/232 |
| 2013/0197575 A1 | 8/2013 | Karapetian et al. | 606/232 |
| 2013/0197576 A1 | 8/2013 | Catania et al. | 606/232 |
| 2013/0197578 A1 | 8/2013 | Gregoire et al. | 606/232 |
| 2013/0197579 A1 | 8/2013 | Foerster et al. | 606/232 |
| 2013/0267998 A1 | 10/2013 | Vijay et al. | 606/232 |

FOREIGN PATENT DOCUMENTS

| | | | | |
|---|---|---|---|---|
| EP | 0 571 686 A1 | 12/1993 | | A61B 2/08 |
| EP | 0 611 557 A2 | 8/1994 | | A61B 2/08 |
| EP | 1 072 234 A2 | 1/2001 | | A61F 2/08 |
| EP | 1 072 237 A1 | 1/2001 | | A61F 2/36 |
| FR | 2777442 | 10/1999 | | A61B 17/04 |
| FR | 2777447 | 10/1999 | | A61B 17/56 |
| JP | 2286468 | 11/1990 | | B62D 1/16 |
| JP | 8-52154 | 2/1996 | | A61B 17/56 |
| JP | 08-206121 | 8/1996 | | A61B 17/04 |
| JP | 11-502437 | 3/1999 | | A61B 17/58 |
| JP | 2000-225118 | 8/2000 | | A61B 17/04 |
| WO | 89/10096 | 11/1989 | | A61B 19/00 |
| WO | 91/06247 | 5/1991 | | A61B 17/00 |
| WO | 95/06439 | 3/1995 | | A61B 17/00 |
| WO | 95/025469 | 9/1995 | | A61B 17/04 |
| WO | 96/28118 | 9/1996 | | A61F 5/00 |
| WO | 97/20522 | 6/1997 | | A61F 2/08 |
| WO | 99/53843 | 10/1999 | | A61B 17/04 |
| WO | 99/53844 | 10/1999 | | A61B 17/04 |
| WO | 02/21997 | 3/2002 | | A61B 17/04 |
| WO | 03/020137 | 3/2003 | | A61B 17/02 |
| WO | 03/049620 | 6/2003 | | A61B 17/04 |
| WO | 2011/060437 | 5/2011 | | A61B 17/04 |

OTHER PUBLICATIONS

PCT Search Report and Written Opinion for PCT/US06/21125 6pgs, Mailed May 22, 2008.
PCT International Search Report for PCT/US01/21905 3pgs, Mailed Jan. 22, 2002.
PCT International Preliminary Examination Report for PCT/US01/21905 3pgs, Oct. 17, 2003.
PCT International Search Report for PCT/US01/17689 3pgs, Mailed Dec. 19, 2001.
PCT International Preliminary Examination Report for PCT/US01/17689 15pgs, Feb. 9, 2003.
PCT International Search Report for PCT/US02/17493 1pg, Mailed Mar. 27, 2003.
PCT International Preliminary Examination Report for PCT/US02/17493 4pgs, Sep. 8, 2003.
PCT International Search Report for PCT/US02/41018 2pgs, Mailed Jun. 5, 2003.
PCT International Preliminary Examination Report for PCT/US02/41018 3pgs, Feb. 22, 2004.
PCT International Search Report for PCT/US02/04231 1pg, Mailed Aug. 14, 2002.
PCT International Preliminary Examination Report for PCT/US02/04231 3pgs, Nov. 13, 2002.
PCT International Search Report for PCT/US03/35695 1pg, Mailed Feb. 14, 2005.
PCT International Preliminary Examination Report for PCT/US03/35695 4pgs, Dec. 21, 2005.
EP Partial European Search Report for EP02742470 3pgs, Apr. 13, 2004.
EP Supplementary European Search Report for EP02742470 5pgs, Jul. 30, 2004.
EP Extended Search Report for EP09162639 4pgs, Oct. 28, 2009.
EP Supplementary European Search Report for EP02792506 3pgs, Mar. 24, 2010.
UK Search Report for GB 0816111.9 3pgs, Dec. 16, 2008.
European Search Report for EP 02734649 3pgs, Jan. 22, 2009.
PCT Search Report and Written Opinion for PCT/US13/33664 10pgs, Jun. 14, 2013.
DE Examination Report for DE 102008046561.5 11 pgs, Nov. 16, 2012.

* cited by examiner

RESTRICTED WEDGE SUTURE ANCHOR AND METHOD FOR SOFT TISSUE REPAIR

FIELD OF THE INVENTION

The present invention relates to an apparatus and method for repairing soft tissue regions. More particularly, the present invention relates to an apparatus and method for adjustably affixing torn soft tissues to a region of bone.

BACKGROUND

It is an increasingly common problem for tendons and other soft connective tissues to tear or to detach from associated bone. One type of tear or detachment is a "rotator cuff" tear, wherein the supraspinatus tendon separates from the humerus, causing pain and loss of ability to elevate and rotate the arm. Complete separation of tissue from the bone can occur if the shoulder is subjected to gross trauma, but typically, the tear begins as a small lesion, especially in older patients.

There are various surgical approaches for repair of the rotator cuff, one known as the "classic open" and another as the "mini-open". The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion.

The mini-open technique differs from the classic approach by working through a smaller incision and splitting rather than detaching the deltoid. Additionally, this procedure is typically performed in conjunction with arthroscopic acromial decompression. Once the deltoid is split, it is refracted to expose the rotator cuff tear. As before, the cuff is debrided, the humeral head is abraded, and the so-called "transosseous tunnels" are "punched" through the bone or suture anchors are inserted. Following the suturing of the rotator cuff to the humeral head, the split deltoid is surgically repaired.

Less invasive arthroscopic techniques continue to be developed in an effort to address the shortcomings of open surgical repair. Working through small trocar portals that minimize disruption of the deltoid muscle, surgeons have been able to reattach the rotator cuff using various suture anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture.

The skill level required to facilitate an entirely arthroscopic repair of the rotator cuff is fairly high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of suture anchors to provide a suture fixation point in the bone, the knots that secure the soft tissues to the anchor by necessity leave the knot bundle on top of the soft tissues. In the case of rotator cuff repair, this means that the knot bundle is left in the shoulder capsule where it can be felt by the patient postoperatively when the patient exercises the shoulder joint. So, knots tied arthroscopically are difficult to achieve, impossible to adjust, and are located in less than optimal areas of the shoulder. Suture tension is also impossible to measure and adjust once the knot has been fixed.

There are various suture anchor designs available for use by an orthopedic surgeon for attachment of soft tissues to bone. A number these designs include use of a locking plug which is forced into a cavity of the anchor body to secure the suture therein. Although there is some merit to this approach for eliminating the need for knots in the attachment of sutures to bone, a problem with being able to properly set the tension in the sutures exists. The user is required to pull on the sutures until appropriate tension is achieved, and then to set the plug portion into the suture anchor portion. This action increases the tension in the sutures, and may garrote the soft tissues or increase the tension in the sutures beyond the tensile strength of the material, breaking the sutures. In addition, the minimal surface area provided by this anchor design for pinching or locking the sutures in place will abrade or damage the suture such that the suture's ability to resist load will be greatly compromised. And, perhaps worse, once the suture is fixed the suture cannot be adjusted or retensioned. This is a shortcoming of such designs because it is not uncommon for a physician to desire to reposition or adjust the tissue location and suture after the anchor has been set.

A suture anchor that addresses some of the shortcomings mentioned above is shown in FIGS. 1A and 1B. Anchor 1 may include a rotatable or pivoting cam 5 to lock suture 28 within suture anchor 1. Suture leg 28a may be bound or connected to tissue (tissue not shown), and suture leg 28b may be free to be adjusted by the practitioner. In FIG. 1A, the bound suture tension (T1) is minimal as the tissue may not be adjacent the anchor 1, and the practitioner is applying open suture tension (T2) to draw the suture 28 around the cam 5 and draw the tissue attached to bound suture leg 28a closer to the suture anchor 1 and into engagement with the bone. As the bound suture tension (T1) increases, due to the tissue being closer to its target location, T1 may begin to approximate or exceed the open suture tension (T2), and the resulting frictional force $F_{(T1+T2)}$ between the cam 5 and the suture 28 may cause the cam 5 to rotate clockwise, and clamp down and lock or wedge the suture 28 as shown in FIG. 1B. Problematically, as the coefficient of friction between the cam 5 and suture 28 decreases (such as, for example, in low friction environments when certain low friction sutures are used, and/or liquids present), the suture 28 may slip and cam 5 may not rotate or the lock force may not be sufficient, i.e. the lock mechanism may have a tendency to fail. This is undesirable.

Thus, a suture anchor device and method for repairing the rotator cuff or fixing other soft tissues to bone, wherein suture tension can be adjusted, released and conveniently retensioned after it is deployed and locked, and that maintains a strong locking force and functions reliably in a low friction environment is desirable. It is also desirable that there is no requirement for the surgeon to tie a knot to attach the suture to the suture anchor, and wherein the procedure associated with the new approach is better for the patient, saves time, is uncomplicated to use, and easily taught to practitioners having skill in the art.

SUMMARY OF THE INVENTION

An anchor device for repairing soft tissue with a suture comprises an anchor body wall defining a lumen through the anchor body. A suture locking wedge is movably disposed at least partially within the lumen. A suture is looped around the suture locking wedge. When a tension force is applied to the tissue limb of the suture, the suture locking wedge is urged into a first position in which the suture is compressed between the suture locking wedge and a first contact location of the anchor body. When a second tension force is applied to the free limb of the suture the suture locking wedge is urged away from the first contact location such that the suture is not compressed.

In one embodiment the anchor device comprises a wedge guide which restricts movement of the suture locking wedge to a path such that when a tension force is applied to the tissue limb of the suture, the suture locking wedge is urged into the first position in which the suture is compressed between the suture locking wedge and a first contact location of the anchor body and such that when a second tension force is applied to the free limb of the suture the suture locking wedge is urged away from the first contact location such that the suture is not compressed. The path comprises a translational dimension and an angular dimension. The multiple directions of freedom of the path increases leverage and clamping force to secure the suture.

The guide may have various structures. In one embodiment the guide comprises a slot and the suture locking wedge has a lateral portion which engages the slot. The slot may be curved, or have an arcuate shape. The slot may have a constant height.

In another embodiment the guide comprises a protrusion from the wall of the anchor body, and the suture locking wedge comprises a recess which is sized to engage and track the protrusion.

In another embodiment the suture locking wedge has a cuboid shape and comprises two opposing substantially planar surfaces.

In another embodiment the suture locking wedge is curved.

In another embodiment the anchor body comprises a bone fixation structure for securing the anchor device in the bone wherein the bone fixation structure is selected from the group consisting of threads, ridges, barbs, and wings.

In another embodiment at least one of the anchor body and the suture locking wedge comprise an elastic section which deforms when the suture locking wedge is placed in the first position.

In another embodiment the first contact location comprises a surface parallel to a longitudinal axis of the anchor body.

In another embodiment the first contact location comprises a surface not parallel to a longitudinal axis of the anchor body.

In another embodiment an anchor device for repairing soft tissue with a suture comprises a suture locking wedge movably disposed at least partially within the anchor device and being in contact with the suture when the suture is threaded through the anchor device and looped around the suture locking wedge. A wedge track guides the suture locking wedge to a first position when a tension force is applied to the tissue limb of the suture in which the suture is compressed between the suture locking wedge and a first contact location of the body and to move the suture locking wedge away from the first contact location when a second tension force is applied to the free limb of the suture such that the suture is not compressed.

In another embodiment the anchor device comprises an anchor body having a wall, and the wedge track comprises at least two slots in the wall of the anchor body and the suture locking wedge has a portion which engages the slots. The slots may be curved.

In another embodiment the suture locking wedge is substantially planar.

In another embodiment the track is curved.

In another embodiment the track comprises a translational dimension and an angular dimension.

In another embodiment the track comprises a recess in the wall of the anchor body.

In another embodiment the track comprises a protrusion from the wall of the anchor body, and the suture locking wedge comprises a recess sized to engage the protrusion.

In another embodiment the anchor body further comprises a bone fixation structure for securing the anchor device in the bone wherein the bone fixation structure is selected from the group consisting of threads, ridges, barbs, and wings.

In another embodiment at least one of the anchor body and the wedge comprises an elastic section which deforms when the suture locking wedge is placed in the first position.

In another embodiment a method for securing soft tissue to bone comprises: (a) securing a first limb of a length of suture to the soft tissue to be attached to the bone; (b) looping the length of suture through an anchor body and around a surface of a movable suture locking wedge; (c) fixing the anchor body within the bone; (d) positioning the soft tissue in proximity to the bone by applying tension to a second limb of the length of suture, such that the length of suture slides around the suture locking wedge, so as to draw the first limb of the length of suture toward the anchor body, thereby drawing the soft tissue toward the anchor body; and (e) moving the suture locking wedge along a wedge path defined in the anchor body such that the wedge moves to a first suture locking position and compresses the length of suture between a first contact location of the wedge and the anchor body.

In another embodiment the wedge is moved in an angular dimension and a translational dimension.

In another embodiment the step of moving the suture locking wedge is carried out by applying tension to the first limb of the suture.

In another embodiment the approximating step is carried out until the soft tissue is moved within a threshold distance from the anchor body, such that a second tension arises on the first limb from the soft tissue.

In another embodiment the step of moving the suture locking wedge is carried out by halting applying the first tension on the second limb, thereby causing the second tension on the first limb of the suture to move the suture locking wedge along the wedge path.

In another embodiment the method further comprises applying tension on the second limb of the suture to unseat the suture locking wedge subsequent to said step (e) to release the suture from being compressed.

In another embodiment the method further comprises repeating steps (d) and (e) to reposition the soft tissue and to re-tension the suture.

In another embodiment applying tension is performed by pulling on the second limb of the suture by hand.

DETAILED DESCRIPTION

Figure 1A:
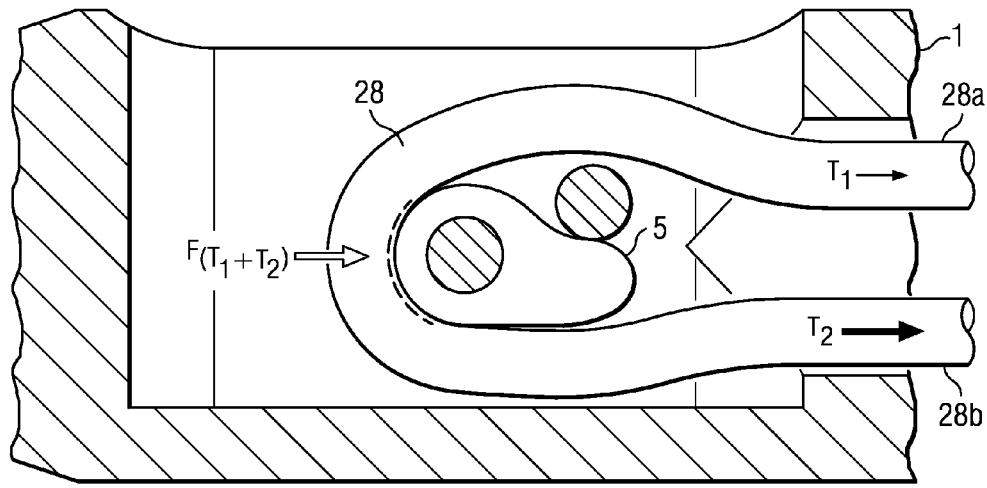
FIGS. 1A and 1B show an example of a suture anchor with a cam, in an open and locked position respectively.
Figure 1B:
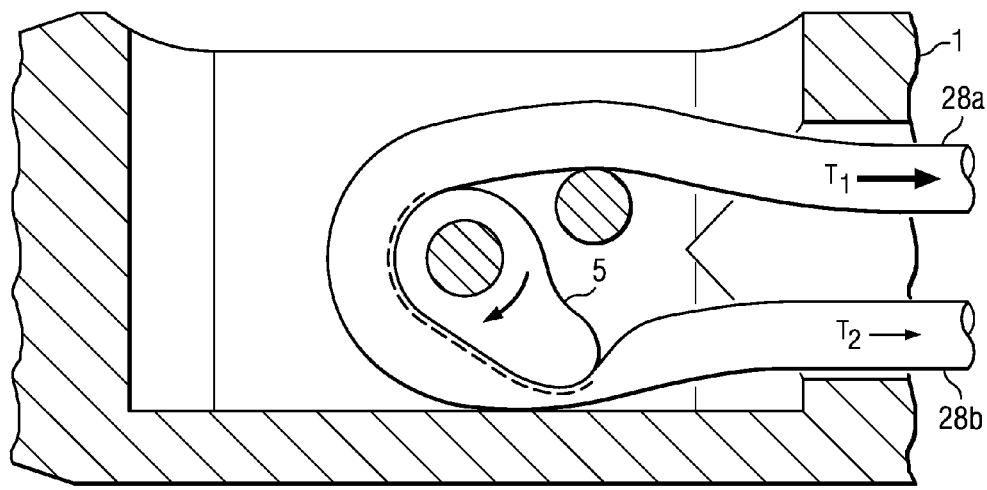

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

The following co-pending patent applications, which are being submitted contemporaneously with the present application, are incorporated by reference in their entirety: U.S. Ser. No. 13/359,631, entitled "ROTATING LOCKING MEMBER SUTURE ANCHOR AND METHOD FOR SOFT TISSUE REPAIR"; U.S. Ser. No. 13/359,642, entitled "FREE FLOATING WEDGE SUTURE ANCHOR FOR SOFT TISSUE REPAIR"; U.S. Ser. No. 13/359,826, entitled "BIASED WEDGE SUTURE ANCHOR AND METHOD FOR SOFT TISSUE REPAIR"; U.S. Ser. No. 13/359,891, "METHOD FOR SOFT TISSUE REPAIR WITH FREE FLOATING SUTURE LOCKING MEMBER", all of which are filed on the same date as the present application, and all of which are commonly assigned to ArthroCare Corporation.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is also to be appreciated that unless defined otherwise, all technical and scientific terms used herein have the same meaning as commonly understood by one of ordinary skill in the art to which this invention belongs.

The present invention provides an improved knotless suture anchor apparatus for anchoring a length of suture with respect to a bone structure. In an exemplary embodiment described herein, the apparatus is used to anchor a length of suture to the humeral bone of the human shoulder. The length of suture is desirably looped through soft tissue, such as a rotator cuff tendon, to approximate and fix the soft tissue with respect to the bone structure. It should be understood, however, that the suture anchor apparatus may be utilized to secure a length of suture to anatomies other than in a bone structure. In this regard, the preferred apparatus includes an anchor body within which the length of suture may be adjusted freely and then anchored or secured without knots. If the anchor body is to be implanted within a body tissue, structure on the anchor's exterior may be provided for securing it therein. In a preferred embodiment, the anchor body is inserted within a bone structure, and a pair of wings are deployed from the exterior of the anchor body to hold it within the cavity.

As mentioned above, the present invention is particularly well-suited for repairing rotator cuff injuries by re-attaching the rotator cuff tendon to the outside of the humeral head. Embodiments of the present invention permit minimally invasive surgeries on such injuries and greatly facilitate rapid and secure fixation of the rotator cuff tendon to the humeral head. However, it should be understood that the same principles described herein apply to the repair of other injuries in which soft tissue is to be re-attached to a bone structure or other tissue region.

Embodiments of the present invention permit the user to insert at least one anchor into bone independently of any other anchor, lock an anchor in the bone, allow the user to subsequently tension or loosen a length of suture or wire between the anchors or between the anchor and soft tissue, to affix the soft tissue, immobilize the suture or wire, release and retension the suture, and then disassociate the inserter assembly from the at least one anchor, leaving the at least one anchor and the soft tissue repaired. Such an anchor inserter assembly may preferably eliminate the need to separately pass suture or wire, eliminate the need to tie knots, allow the procedure to be performed without the need to move an arthroscope from an articular side to a bursal side of the cuff, and by virtue of the small diameter of the anchor implants, reduce the size of the hole placed in any tissue, if passing the implant through.

Anchor Structure Overview

Figure 2A:
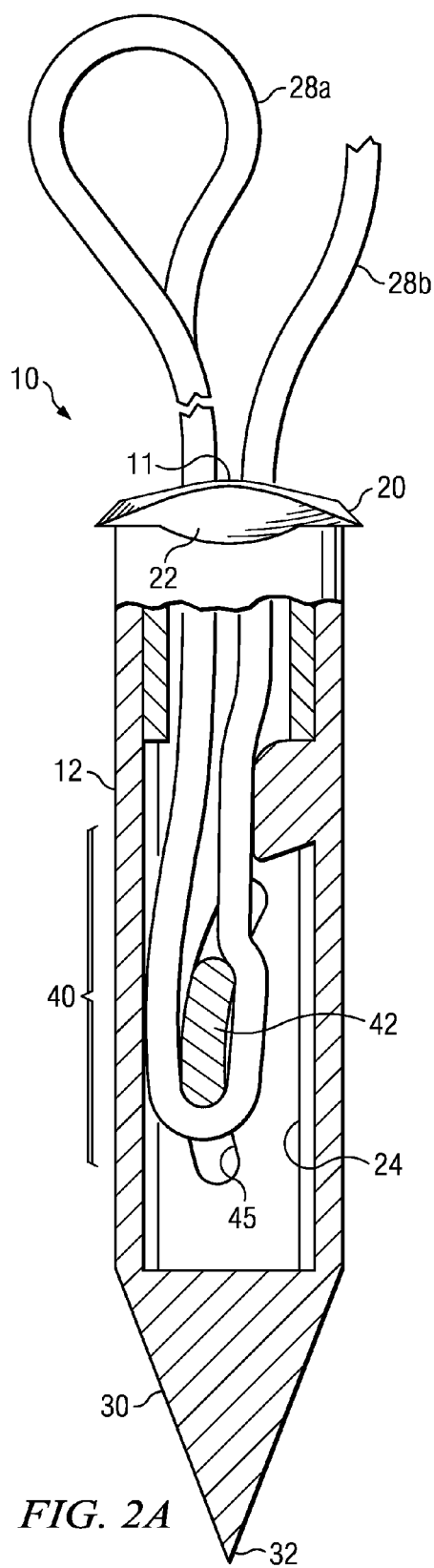
FIGS. 2A and 2B show a suture anchor with a suture locking wedge in an open and locked position respectively.
Figure 2B:
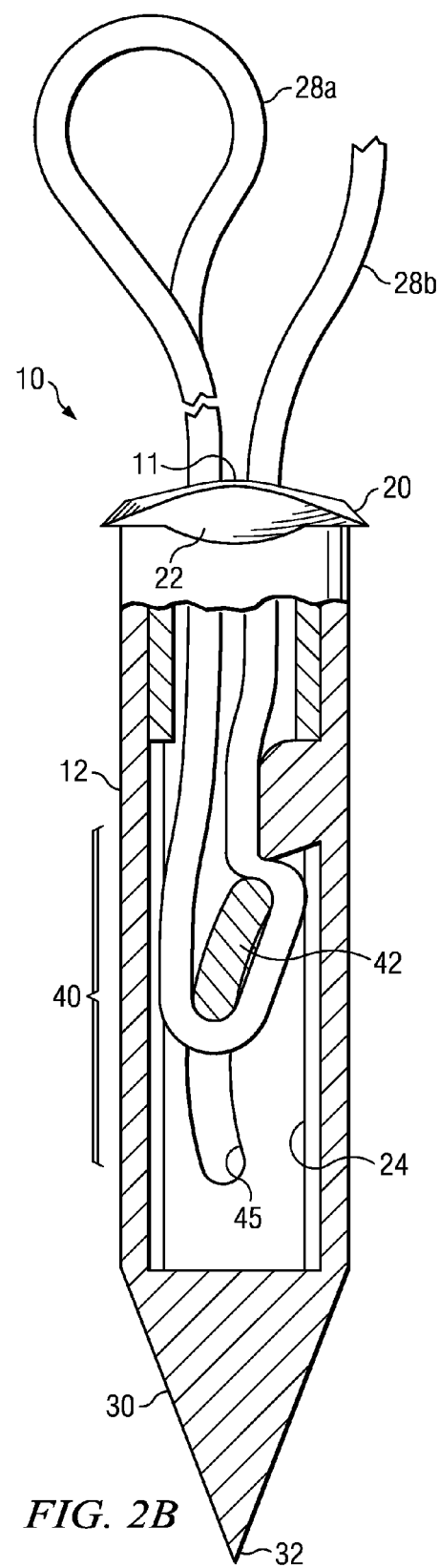

FIGS. 2A and 2B illustrate a suture anchor device 10 including a body 12 which includes a cavity or lumen 24, and a second component, namely, suture locking wedge 42 which is positioned within the lumen 24 of the outer anchor body. The suture locking wedge 42 is adapted to movably cooperate with the anchor body 12 to lock and release a suture 28 by compressing the suture between the anchor components. In particular, anchor body 12 includes tracks or slots 45 which guide the suture locking wedge from an unlocked open configuration to a locked configuration as will be discussed in more detail herein.

In the embodiment shown in FIGS. 2A and 2B, the lumen 24 commences at a proximal aperture or opening 11, and extends distally along the longitudinal axis of the anchor body 12. The axial lumen 24 is shown as being substantially cylindrical. However, the shape of the lumen or cavity may vary.

At least one suture 28 which includes at least one bound leg 28a is shown threaded through the opening 11 and extends distally through the lumen 24, around the suture locking member or wedge 42, and may subsequently be redirected proximally back through the lumen 24 and out of opening 11 to result in a free leg 28b. The bound side or leg 28a is considered bound because in practice, this leg or limb of the suture is "bound" to the soft or connective tissues to be attached to the target tissue such as bone by virtue of passing the sutures through the connective or soft tissues using conventional suturing techniques known in the art. The free side or leg 28b is considered "free" because the surgeon or practitioner, in practice, has control over this limb or leg of the suture with his or her hands or appropriate instrumentation.

Suture Locking Wedge

The suture locking wedge 42 is movably disposed within the lumen 24 of the anchor body and in particular, is engaged with the slots 45. The tracks or slots 45 guide and restrict movement of the suture locking wedge to substantially translational and angular movements as shown. In a first or open configuration as shown in FIG. 2A, suture locking wedge 42 is operable to allow suture free leg 28b to be pulled so that the suture may slide freely around suture locking wedge 42 and into, out of, and through suture locking portion 40 so as to pull soft tissue attached to the bound leg 28a closer to suture anchor 10. Once a sufficient amount of tension is present on the bound leg 28a, the surgeon may adjust (e.g., release, reduce or halt) the tension on the free limb 28b so as to cause the suture locking wedge 42 to move. The wedge moves in multiple directions (e.g., axially and angularly) until it reaches a locking position shown in FIG. 2B thereby compressing the suture 28 against a portion of the anchor body 12.

The shape of the suture locking wedge may vary. The suture locking wedge need not have one side or edge thicker than another. Indeed, the suture locking wedge may have, but need not be limited to, a cuboid-like shape. The suture locking wedge may have an arcuate shape and parallel surfaces as shown in FIGS. 2A and 2B. Non-limiting examples of cross sectional shapes of the suture locking wedge includes square, rectangle, trapezoidal, oval, arcuate, triangular, and parallelogram.

Suture locking wedge 42 may preferably have a smooth surface, and more specifically, a smooth distal surface to allow for easy suture sliding around the suture locking wedge surface during use. Additionally, the suture locking wedge 42 may have an elongate nest or groove (not shown) to provide some limitation to any lateral motion of the suture 28 (i.e. to keep the suture 28 from slipping off the suture locking wedge 42). The suture 28 itself may also comprise a low friction material such as polyester suture to create an overall low friction environment. Examples of sutures include without limitation low friction UHMWPE suture and polyester suture.

The suture locking wedge may be formed of (or comprise) metal, polymer, or another material. In a preferred embodiment, the wedge is formed from a rigid, relatively low friction material, so as to allow easy sliding of the suture. Additionally, elastic or resilient materials or components may be incorporated into the suture locking wedge and/or the anchor body. As the suture locking wedge is urged into a locked configuration, the elastic component(s) tend to conform to one another which can increase the clamping force on the suture.

Wedge Guide and Slots

As mentioned above the anchor body 12 preferably includes at least one track or slot 45 to guide the suture locking wedge between an open suture or unlocked configuration and a locked configuration. The slot 45 is shown extending through the wall of the anchor. However, the slot need not extend completely through the wall. The slot or window may be covered or closed.

The slot 45 is also shown having an arcuate, elongate shape. However, the shape of the slot may vary. Additionally, the size of the slot may vary. An exemplary length of the slot ranges from 2 to 10 mm. An exemplary height of the slot ranges from 0.5 to 3 mm. However, these ranges are not intended to be limiting except where specifically recited in the appended claims. Preferably, the slot has a size and shape that provides a track to the suture locking wedge 42, or to a portion or projection of the suture locking wedge member. The track may have a translational component, and an angular component with respect to the longitudinal axis of the anchor body. The guide or track may be linear or non-linear. The path of the suture locking wedge is optimized to provide enhanced leverage and compression on the suture in the locked position. As shown, the suture locking wedge travels along the arcuate path defined by slots 45 until it reaches the locked position, compressing the suture 28. Further details of the suture locking are discussed below in connection with FIGS. 3A and 3B.

The anchor body 12 may comprise additional openings or apertures (not shown). For example, apertures may be provided for the purpose of providing space or room for suture routing. Suture routing, in some instances, requires the suture to be doubled up around a preloaded snare type device (not shown), and pulled through the anchor. More space at the locations along the suture path where the suture turns is desirable. To this end, apertures are positioned at locations along the suture path where the suture changes direction. The apertures are preferably sized to be at least as wide as the suture diameter. However, the shape, size and location of the apertures may vary. When the anchor is loaded with a suture, for example, a portion of the suture 28 may protrude or ride outside of the anchor body. Alternative embodiments may have additional apertures elsewhere on the anchor body such as, for example, on the opposite or inferior side of anchor 10 (not shown).

The distal end section 30 of suture anchor 10 may comprise a piercing tip 32 to penetrate soft tissue and be driven into and through tissue and bone. The piercing tip may facilitate the anchor to be pounded or driven into bone with a mallet or hammer-like instrument. Piercing tip 32 may be hollow or solid depending on strength or weight requirements and manufacturing technique. Suture anchor 10 may be preferably fabricated from a metal such as 316L stainless steel, although other materials such as titanium may be used. Alternative embodiments may include a blunted tip for inserting into a prepared bone passage or a threaded or tissue cutting tip.

After the anchor is positioned within the target tissue, namely bone, the anchor is fixed within the target tissue so as to remain in place. The suture anchor of the present invention may incorporate a number of features or structure to achieve a bone lock including, for example, assuming a larger profile using a variety of anchoring means such as expansion ribs, molybolts, rivets, wings, and other mechanisms. Alternate embodiments may include a threaded, ridged or barbed portion on the outer surface 12 to lock into the wall of the target tissue (not shown). In one embodiment, proximal end 20 may include an anchoring element with two deformable wings 22 that may be permanently or reversibly deformed or outwardly deployable to have a larger profile so as to anchor or fix the suture anchor 10 within the target tissue.

Suture Locking Detail

Figure 3A:
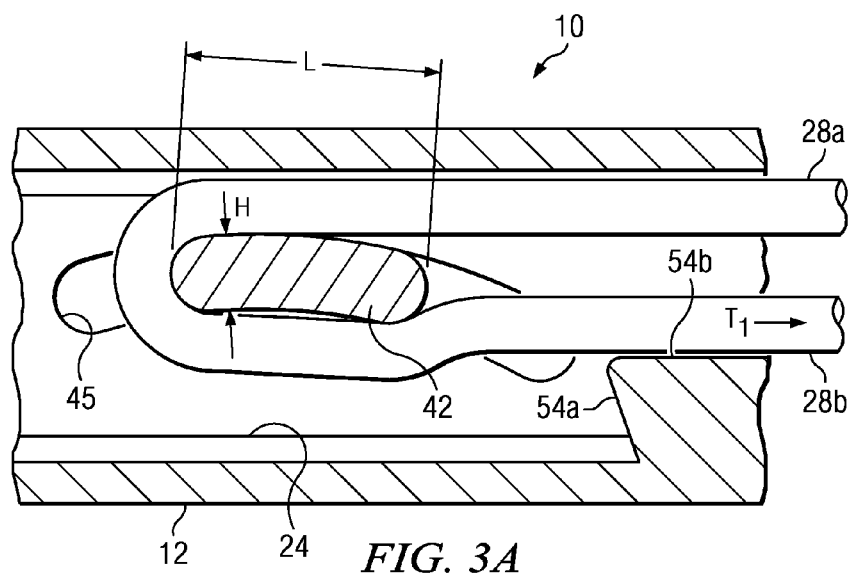
FIG. 3A shows a partial cross sectional view of the suture locking region shown in FIG. 2A corresponding to an unlocked suture configuration.
Figure 3B:
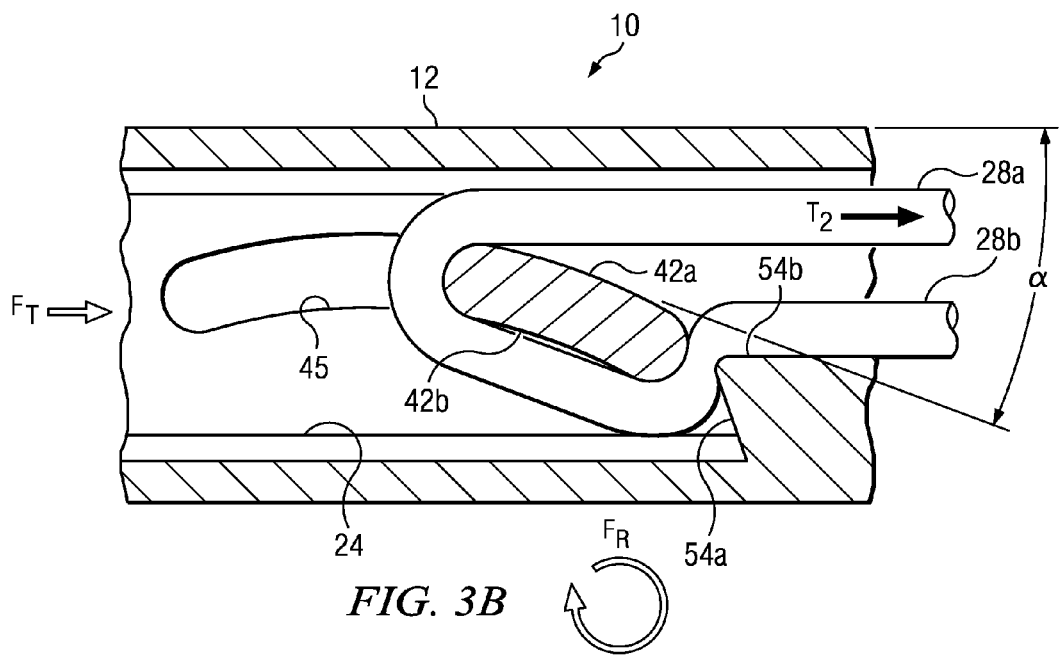
FIG. 3B shows a partial cross sectional view of the suture locking region shown in FIG. 2B corresponding to a locked configuration.

FIGS. 3A and 3B are enlarged cross sectional views of the anchor device in an open suture configuration and a locked configuration respectively.

With reference to FIG. 3A, the suture locking wedge 42 is shown spaced from contacting surfaces 54a, 54b of the anchor body 12. Suture 28 is shown entering lumen 24, extending around a distal surface of suture locking wedge 42, and returning proximally. In the unlocked or open configuration shown in FIG. 3A, the suture is free to slide around suture locking wedge 42. A tension (T1) may be applied to suture free end 28b as locking member 42 remains in an open position such that the practitioner may slidingly draw suture 28 around suture locking wedge 42. Consequently, tissue connected to the tissue side or bound leg 28a is positioned or approximated towards the anchor as desired.

In the open configuration, slots 45 are shown holding the suture locking wedge 42 in a substantially lateral or horizontal position. Maintaining the suture locking wedge 42 in a near lateral position facilitates routing the suture through the anchor because this position provides a larger space between the wedge surface and the lumen wall 24. Suture routing in some instances requires the suture to be doubled up around a preloaded snare type device (not shown), and pulled through the anchor. More space at the locations along the suture path where the suture turns is desirable.

FIG. 3B shows suture anchor 10 in a locked position. In particular, suture locking wedge 42 is shown positioned proximally, compressing suture 28 between an edge surface of the locking wedge 42, and a suture contacting surface 54b of the anchor body 12. The embodiment in FIG. 3B also includes a second locking surface 54a which is off-axis, namely, not parallel to the longitudinal axis of the suture anchor body. The combination of contact surfaces to compress the suture aid to lock the suture and prevent slip. The combination of contact surfaces at angles to one another creates a tortuous path, increasing frictional forces on the suture.

The suture locking wedge is manipulated into the locked position by manipulation of the suture legs. More specifically, as tension (T2) grows on suture leg 28a due to tissue approximation, and the surgeon releases or modifies the tension on the free limb 28b, the suture locking wedge 42 is moved proximally along slot 45 as shown in FIG. 3B. A force $F_T$ in the translational or axial direction is thus applied the suture locking wedge 42 urging it proximally and against the locking surfaces 54a, 54b.

In addition to the translation force $F_T$, a second type of force or motion is applied to the suture locking wedge 42 when tension on the tissue bound suture leg arises. Because the suture locking wedge is guided along a track or path which forms an angle or curve with respect to the longitudinal axis of the anchor body, the suture locking wedge has at least a second degree of motion or freedom. A rotation force $F_R$ on the suture locking wedge 42 therefore arises. This force $F_R$ urges the wedge in a clockwise direction, and acts to further compress the suture against the suture contacting surfaces as the tissue bound suture leg is placed in tension. The locking or compression on the suture increases as the tension T2 is increased because of the translation, and rotational forces placed on the suture locking wedge 42.

A number of parameters serve to increase the compression and clamping force on the suture including but not limited to the angle ($\alpha$) which the suture locking wedge makes with the longitudinal axis of the anchor body (this is also restricted or controlled by the shape of the slots/tracks), the length of the suture locking wedge (L), and the contacting surfaces of the anchor body. The angle ($\alpha$) guides the suture locking wedge in an angular dimension or movement. The slot also has an axial or translational dimension.

Preferably the angle ($\alpha$) ranges from 5 to 60 degrees, and more preferably is about 20 degrees from the longitudinal axis of the anchor body. The length (L) of the suture locking wedge preferably ranges from about 1 to 10 mm and more preferably is about 5 mm. The width (W) of the suture locking wedge preferably ranges from about 2 to 7 mm and more preferably is about 3 mm. Preferably the width (W) is sufficient to engage the slots and yet not protrude or extend beyond the exterior surface of the anchor body. The thickness or height (H) of the suture locking wedge preferably ranges from about 0.5 to 3 mm and more preferably is about 0.8 mm. The shape of the suture locking wedge and in particular the length (L) serves to increase the rotational or moment force on the wedge. An increased length generally increases the clamping force.

The position or point at which the suture locking wedge compresses the suture against the anchor body, namely, the contacting surface, also affects the frictional forces, and clamping force on the suture. In particular, an off-axis contacting surface such as 54a can increase the frictional force and the clamping force. Further, a combination of contact surfaces 54a, 54b serves to create a corner or more tortuous suture path which also serves to increase the friction or clamping force.

Utilizing a combination of the above described parameters, the suture anchor of the present invention guides a suture locking wedge to a locked configuration. The anchor body cooperates with the suture locking wedge to move the wedge with multiple degrees of motion or freedom. Consequently, the suture locking wedge of the present invention can apply a greater clamping force than that a standard plug or cam having only one degree of freedom. Additionally, as discussed below, the anchor may be conveniently implanted, tensioned, locked, and retensioned as desired.

Anchor Implantation Using Instrument

Figure 4A:
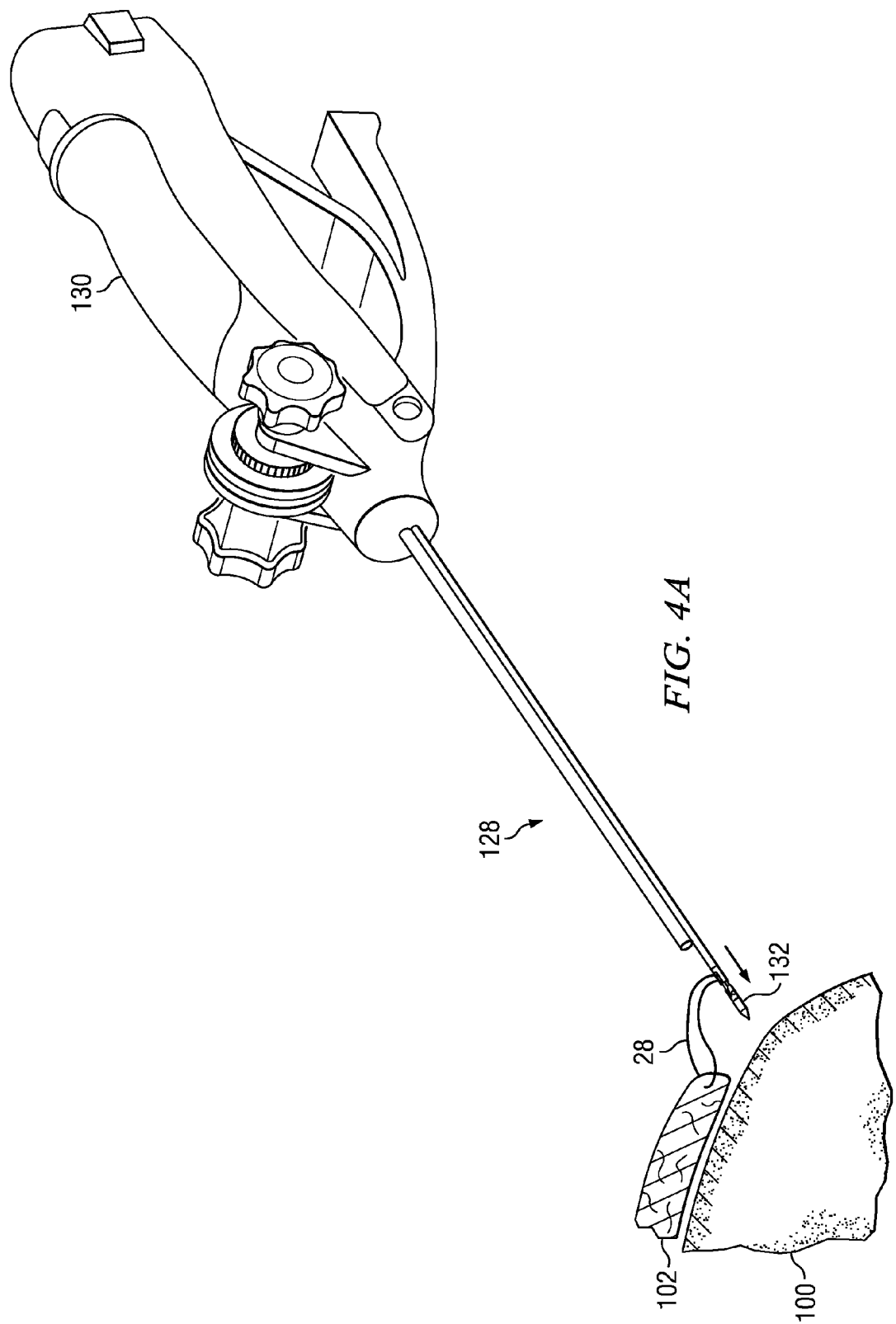
FIGS. 4A, 4B and 4C show a representation of a method of inserting and anchoring a suture anchor in a bone.
Figure 4B:
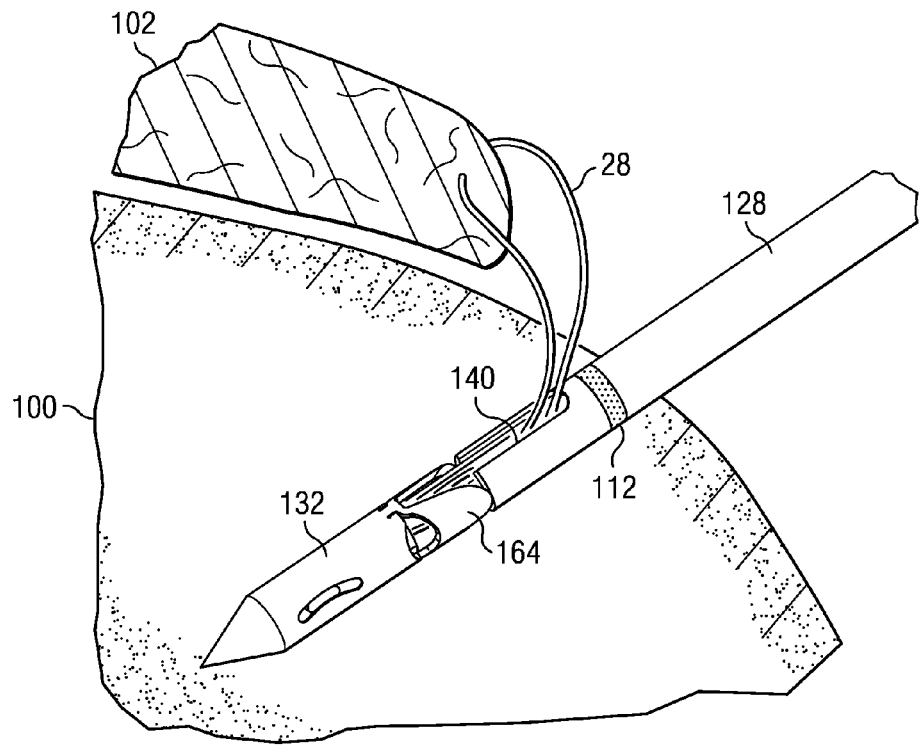
Figure 4C:
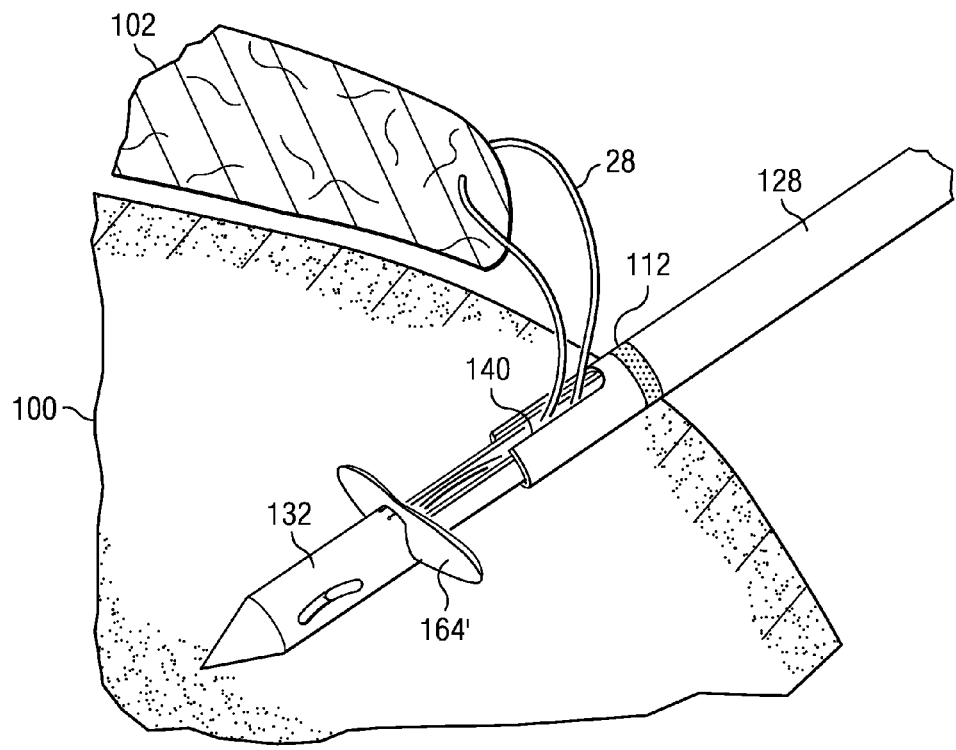

FIGS. 4A, 4B and 4C illustrate a suture anchor being implanted. As shown, suture 28 may be previously stitched, connected to or looped through tissue 102 and preassembled within anchor 132 (e.g., routed through the anchor using a snare) and instrument 128. The stitching process may be accomplished by any known means, and any known suture stitch may be employed. A stitch is desirably secured so that the suture is not inadvertently separated from the tendon after completion of the repair procedure, necessitating re-entry to the surgical site. In preferred approaches, the suture is attached to the soft tissue using a "mattress stitch," which is well known in the art as being a particularly secure stitch which is unlikely to fail postoperatively.

Anchor 132 may then be brought into contact against the underlying bone region 100 using instrument handle 130. Now with reference to FIG. 4B, the proximal end of the instrument 128 or handle 130 may be tapped, e.g., by using a mallet, to drive the suture anchor 132 into the bone at a depth of, for example, approximately 6 mm. If viewed through an arthroscope, primary anchor 132 may be driven into the underlying bone 100 until an anchor depth indicator 112 (e.g., a colored marking or gradation) is visible just above or at the bone 100. Depth indicator 112 is a visual indicator to the user that the appropriate depth for anchor insertion has been reached. This may indicate that the anchor wings 164 have been inserted at the correct depth. Instrument 128 may also have lateral aperture or opening 140, located at the distal portion of the instrument but proximal to anchor wings 164, operable to allow passage of suture 28 from tissue 102 into the anchor. Suture 28 may then extend distally from aperture 140 within anchor 132, around a suture locking wedge (not shown) and return proximally within instrument (not shown) and may connect with a portion of the instrument handle 130, operable for managing the suture 28 during insertion and tensioning.

With suture anchor 132 suitably implanted, the anchor wings 164' may be deployed within the bone 100 using instrument 128, to lock the position of anchor 132 and to prevent or inhibit anchor 132 from being pulled out of bone 100, as shown in FIG. 4C. Anchor 132 may then be released from instrument 128, which may be achieved by a variety of mechanical means, operable to have a weakness or failure point that fractures or disconnects upon application of a force or torque. Some methods for this release are described in U.S. Pat. No. 6,585,730, which is hereby incorporated by reference in its entirety. Also, it is to be understood that a wide variety of structures may be included with the suture anchor to implant the anchor in bone including without limitation barbs, ridges, threads, etc. Aspects of an instrument and method described in U.S. Patent Application Publication No. 2009/0069823 (which is hereby incorporated by reference in its entirety) may be used to insert and deploy anchor 132. Additionally, the anchor may be implanted in other manners, and without a sophisticated instrument as described above.

Figure 5A:
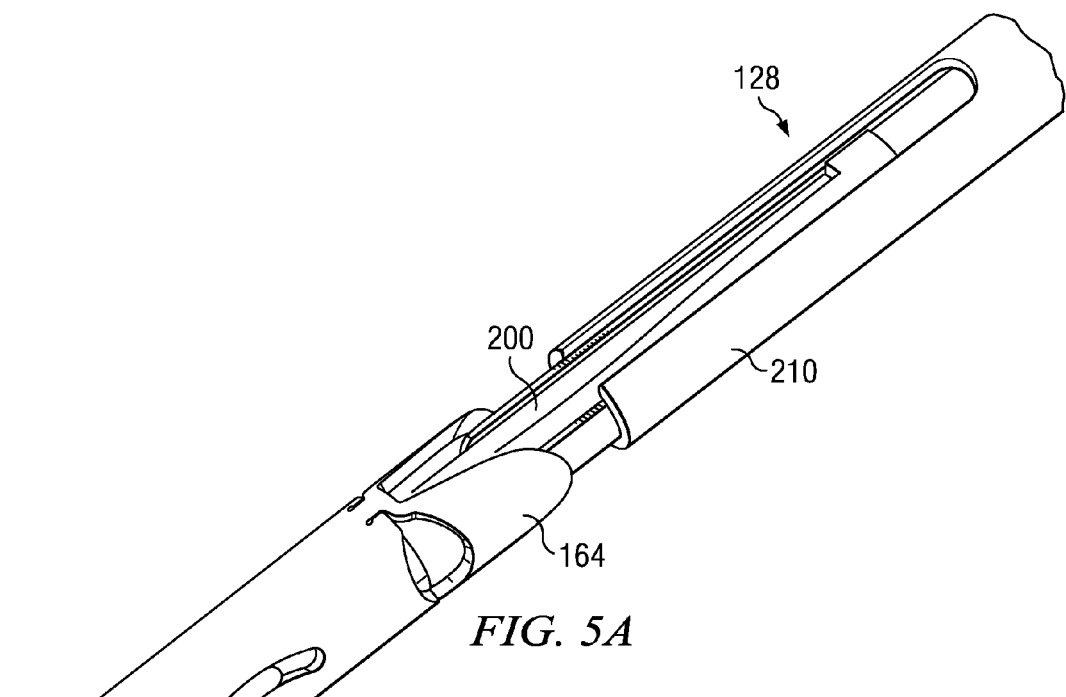
FIG. 5A illustrates a suture anchor deployment method.

FIG. 5A shows one embodiment of an instrument distal end that may be used to deploy or activate anchoring structure. A similar instrument is described in more detail in US Patent Application Publication No. 2010/0191283, which is hereby incorporated by reference in its entirety. Instrument 128 includes a shaft 200, die or driver 210 that moves relative to the anchoring structure 164 so as to urge the anchoring structure radially outwards.

Figure 5B:
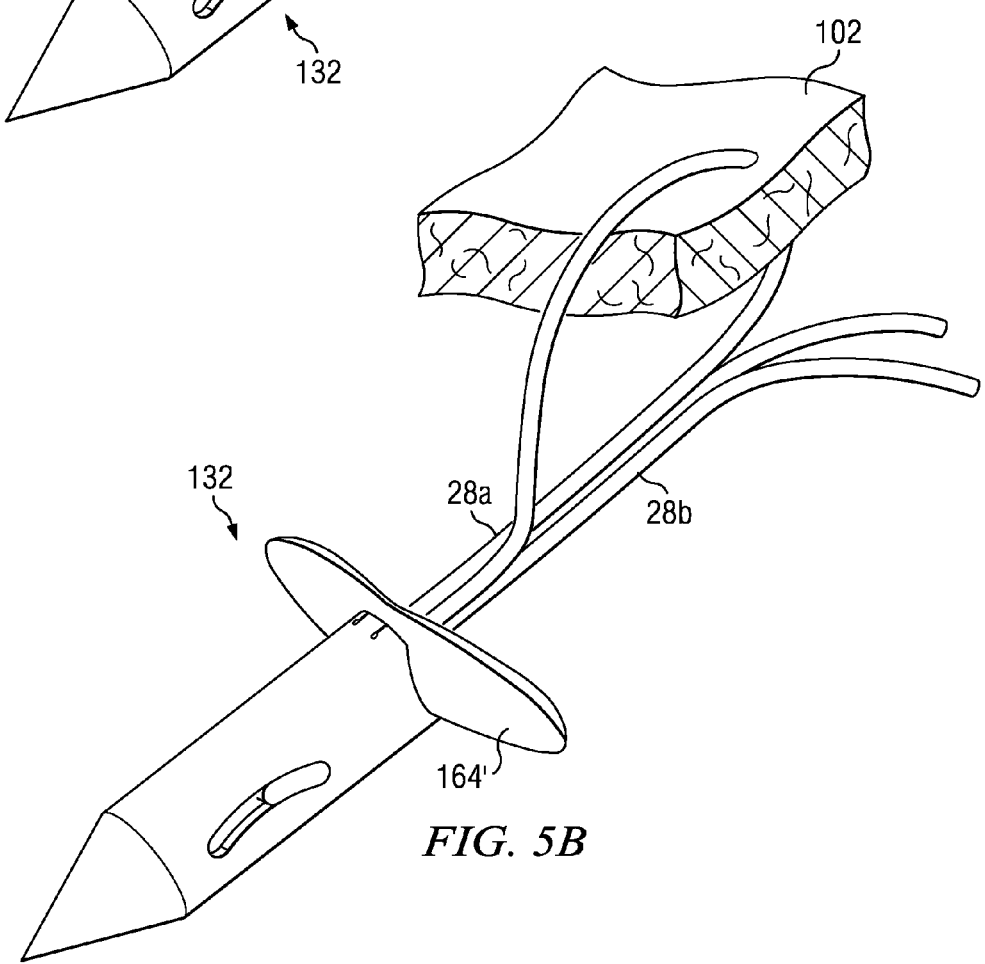
FIG. 5B illustrates the suture anchor shown in FIG. 5A with the anchoring structure deployed and the suture connected with tissue.

FIG. 5B shows a deployed anchoring structure 164' with the bone passage or body cavity removed for clarity. Suture 28a is stitched in a suitable manner to a portion of soft tissue 102, such as a tendon, which is to be secured to a bone (not shown). Suture 28 then extends distally through anchor lumen around suture locking wedge and then returns proximally so as to leave a free end 28b. The free end 28b may extend within instrument (not shown) to manage the suture free end 28b during anchor 132 insertion and deployment.

Figure 6A:
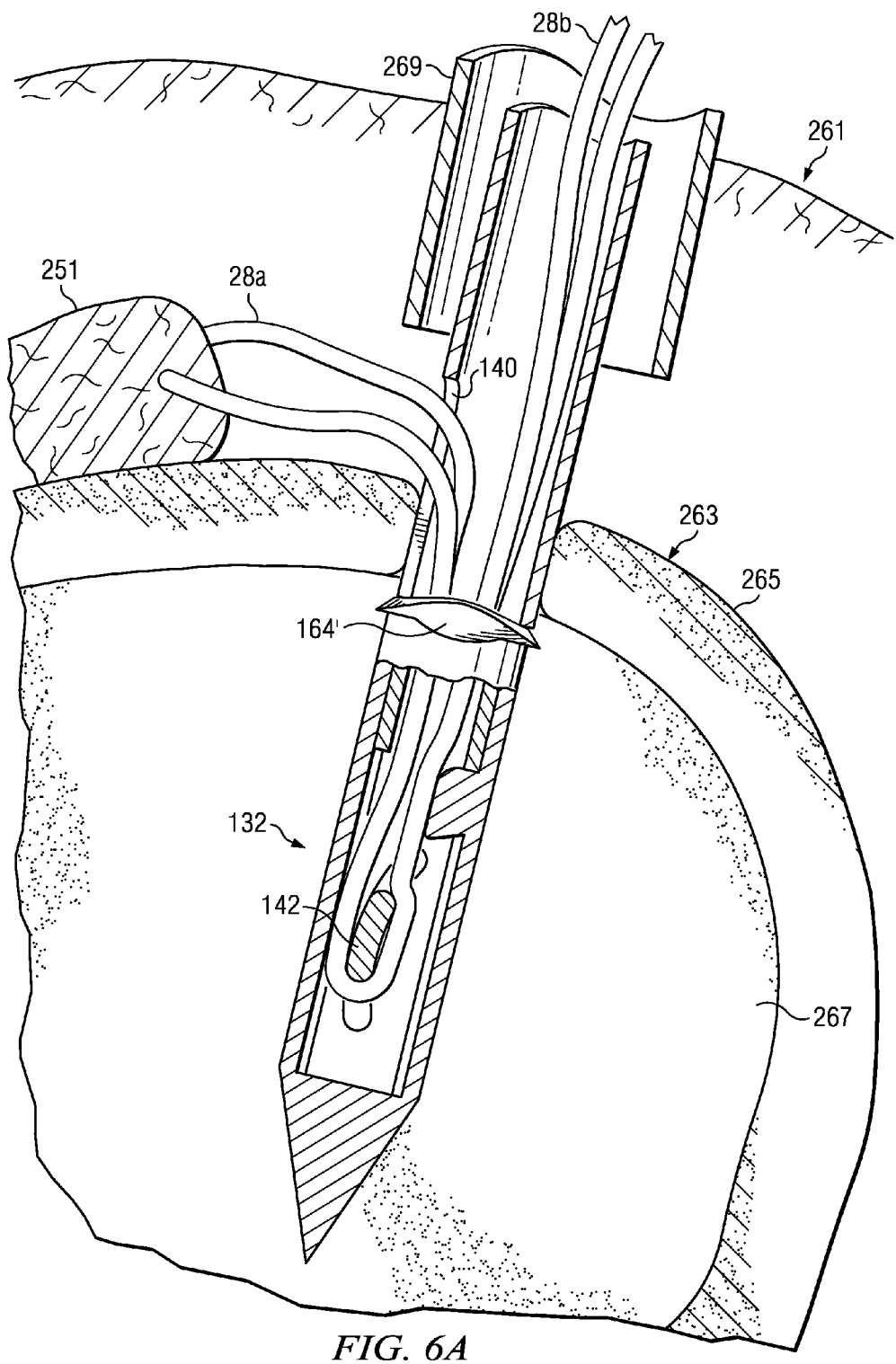
FIGS. 6A and 6B illustrate a method of using a suture anchor in rotator cuff tissue.

FIG. 6A shows a cross section of anchor 132 similar to the anchor described in FIGS. 2 and 3. Anchor 132 is shown within bone tissue 267 and with anchoring structure 164' deployed in the bone. The bone tissue 267 is that of a shoulder 261, which comprises a humeral head 263, including an outer cortical bone layer 265, which is hard, and inner cancellous bone 267, which is relatively soft. As is typically the case for rotator cuff injuries, in this instance the supraspinatus tendon 251 has become separated from the humeral head 263. It is desirable to reattach the tendon 251 to the humeral head 263. Alternate rotator cuff repair procedures are also discussed in U.S. Pat. No. 6,524,317, and entitled "Method and Apparatus for Attaching Connective Tissues to Bone Using a Knotless Suture Anchoring Device", which is hereby incorporated by reference in its entirety.

To effect the rotator cuff repair, the practitioner may first create an incision in the patient's shoulder 261, into which may be inserted a trocar 269, as shown in FIG. 6A. The trocar 269 permits access to the procedural site for visualization instruments, as well as working instruments, and permits the procedure to be completed arthroscopically. Anchor 132 may then be connected with suture 28 and then inserted according to methods described herein. Insertion to the cortical layer 267 is important to ensure anchoring structure 164' gains good purchase on the bone. FIG. 6A shows anchoring structure 164' deployed, at which point the deployment instrument may be disconnected from the anchor 132 as discussed earlier and removed from the site.

Figure 6B:
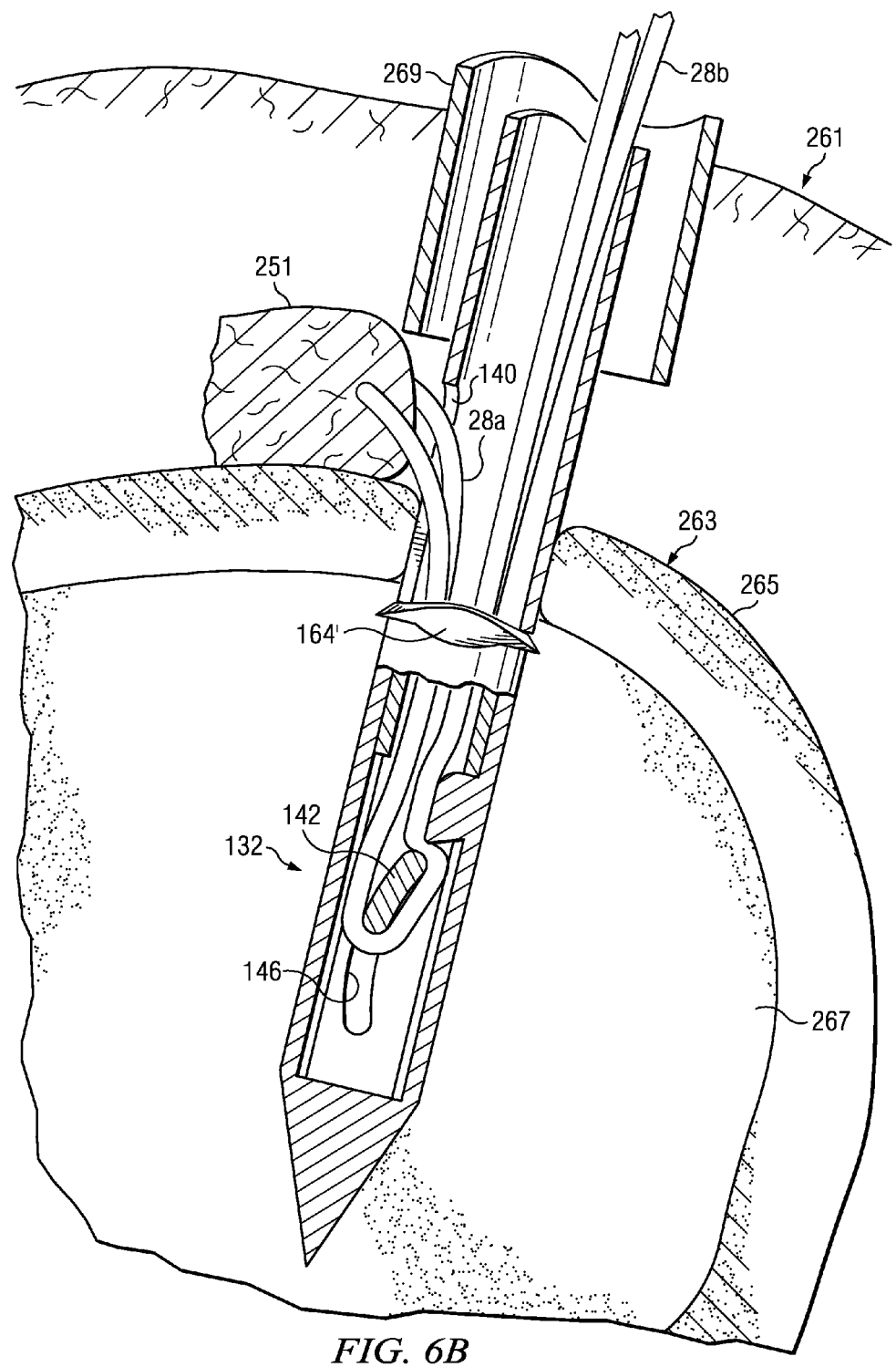

With reference to FIG. 6A, suture locking wedge 142 is shown in an open position, meaning that the suture free end 28b may be freely tensioned or withdrawn proximally to draw tissue 251 to the correct location for reattachment to the bone. As discussed herein, the bound leg or legs 28a of the suture have been connected with the tissue or tendon 251 and may extend through a lateral aperture 140 in the delivery instrument 128 to gain access to the suture anchor 132, about the suture locking wedge 142, until such time as the tendon 251 binding in the bound leg 28a of the suture 28 creates a tension in the suture 28. This will occur when the tendon 251 has been drawn toward the anchor 132 as shown in FIG. 6B, and is itself under appropriate tension for an anatomically proper repair and otherwise snugly situated with respect thereto. Non-limiting examples of threshold distances between the tissue 251 and the proximal end of the anchor range from 2-8 mm and more preferably 3-6 mm. The suture may be drawn by hand, by instrument, or a combination thereof.

Once the tension on the bound limb 28a is present, the practitioner may release or otherwise modify the tension on the free limb 28b so as to allow the tension in the suture bound leg 28a to move the suture locking wedge 142. In the embodiment shown in FIGS. 6A and 6B, the suture locking wedge 142 moves in angular and translational directions along slot 146 to the locked position as shown in FIG. 6B.

Reversibility

The suture locking mechanism of the present invention may be reversible. Retensioning may be possible to permit the continued adjustability of the bound end 28a by applying tensile force to the free end 28b of the suture. This is useful as a surgeon will often find that, during the course of a procedure, after the tendon/soft tissue 251 has been brought into what is believed to be a desired position relative to the bone to which it is being secured, and the suture 28 has been locked into place to retain the tendon in that orientation, a further adjustment is necessary or desired to optimize the outcome.

For example, after the free end 28b has been pulled proximally sufficiently such that a tension is created in the bound end 28a (due to approximation of the tendon 251 to the bone 263), and the suture 28 is locked by the suture locking wedge 142, the bound end 28a is anchored in a fixed position. This ensures that the tendon is not movable relative to the bone after completion of the procedure. However, if the practitioner requires the suture locking wedge to be unlocked, the practitioner may do so by applying sufficient tension on the free end 28b, (possibly also in combination with releasing tension on the bound legs 28a) so as to permit adjustment of the size of the suture loop through the tendon 251, which in turn permits adjustment or fine tuning of the position of the tendon 251 with respect to the bone. The practitioner may make these adjustments by hand or using an instrument.

Once the tendon 251 is adjusted to the desired location, the suture 28 may then be considered locked and the free end 28b may be trimmed near the proximal end of the anchor portion 164', and the incision is closed.

Repeated stress or use of the tendon after the surgery may tend to move or dislodge the suture locking wedge. However, the novel designs of the present invention, and in particular, the ability of the suture locking wedge to move in multiple directions (e.g., angular, axial, and/or rotational) serves to prevent dislodgement of the suture locking wedge. When tension on the tissue bound end 28a increases, the suture locking wedge is leveraged to put an increased compression force on the suture 28. This is one advantage of the present invention even in low friction environments.

Alternative Embodiments

Figure 7A:
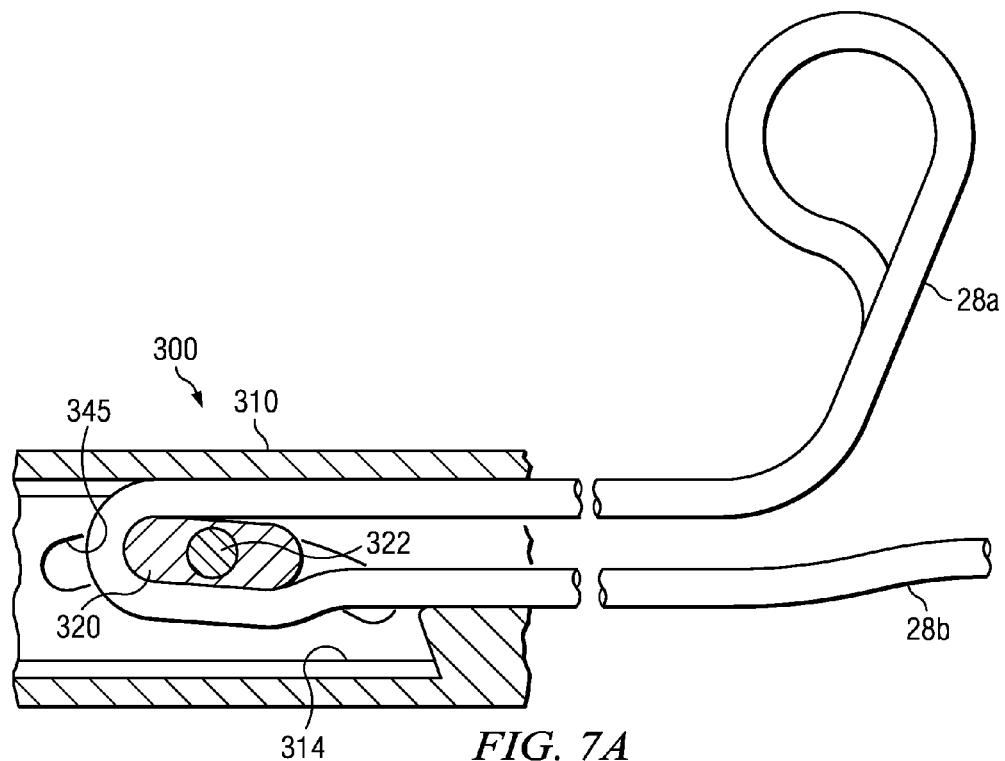
FIGS. 7A and 7B illustrate another suture anchor.
Figure 7B:
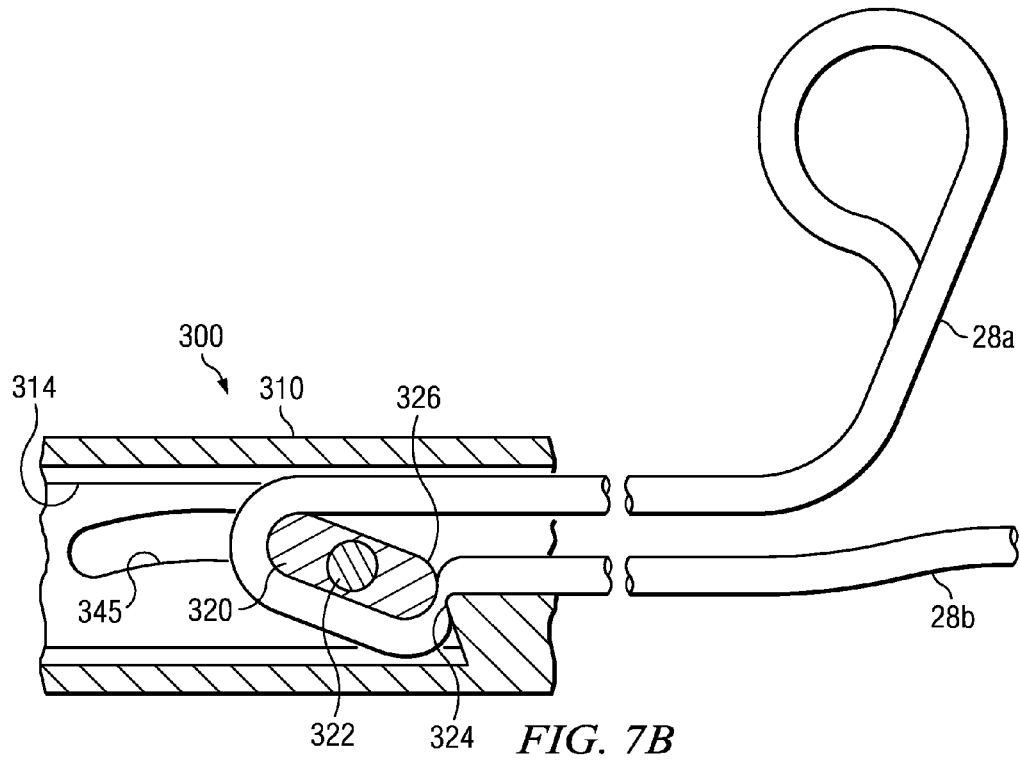

FIGS. 7A and 7B illustrate another suture anchor 300 including an anchor body 310 defining a lumen 314, and a suture locking wedge 320 movably disposed in the lumen. The suture anchor is shown in an open or unlocked configuration in FIG. 7A, and a suture locked position in FIG. 7B. Except for pin 322, a number of the components of the suture anchor 300 are similar to that of the suture anchor 10, described above in connection with FIGS. 2A and 2B.

With reference to FIG. 7A, a pin is shown extending laterally from the edge of suture locking wedge 320. The pin 322 is received and guided by slot 345 instead of the wedge itself. The pin may be an extension of the wedge or it may be a separate component (e.g., a steel pin) fastened to the wedge 320. In one embodiment the wedge is rotatable about the pin. In another embodiment the wedge is fixed relative to the pin. The pin 322 may have various shapes such as for example a projection, extension or indent. The pins preferably do not protrude beyond the exterior surface of the anchor body.

In the unlocked or open position shown in FIG. 7A, the suture locking wedge 320 is held in a near horizontal position. As described above, holding the suture locking wedge in a substantially horizontal or lateral position, in combination with maintaining a large gap or space for the suture to be routed, is desirable. Additionally, although not shown, the anchor body wall 310 may have apertures to provide additional space for the suture to be routed around the suture locking wedge. Portions of the suture may reside outside or outboard of the anchor body. Therefore, the suture need not be confined to the lumen as it is routed around the suture locking wedge.

With reference to FIG. 7B, the suture anchor 300 is shown in a locked configuration. The suture locking wedge 320 is shown compressing the suture against a suture contacting surface 324 of the body 310.

Figure 8A:
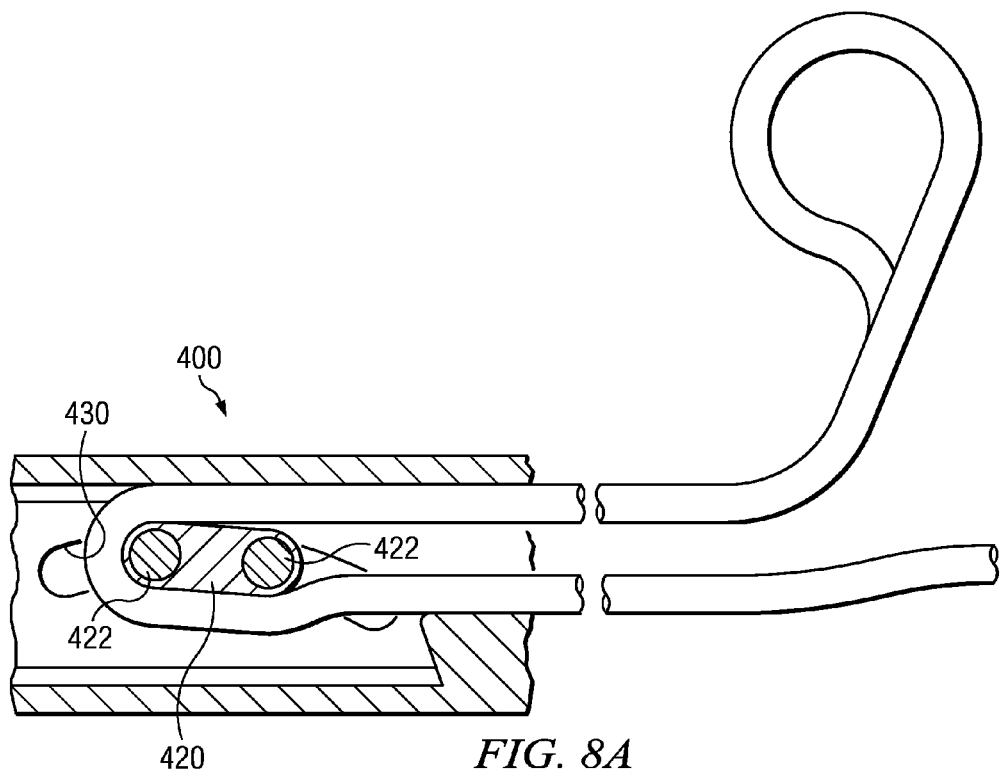
FIGS. 8A and 8B illustrate another suture anchor.
Figure 8B:
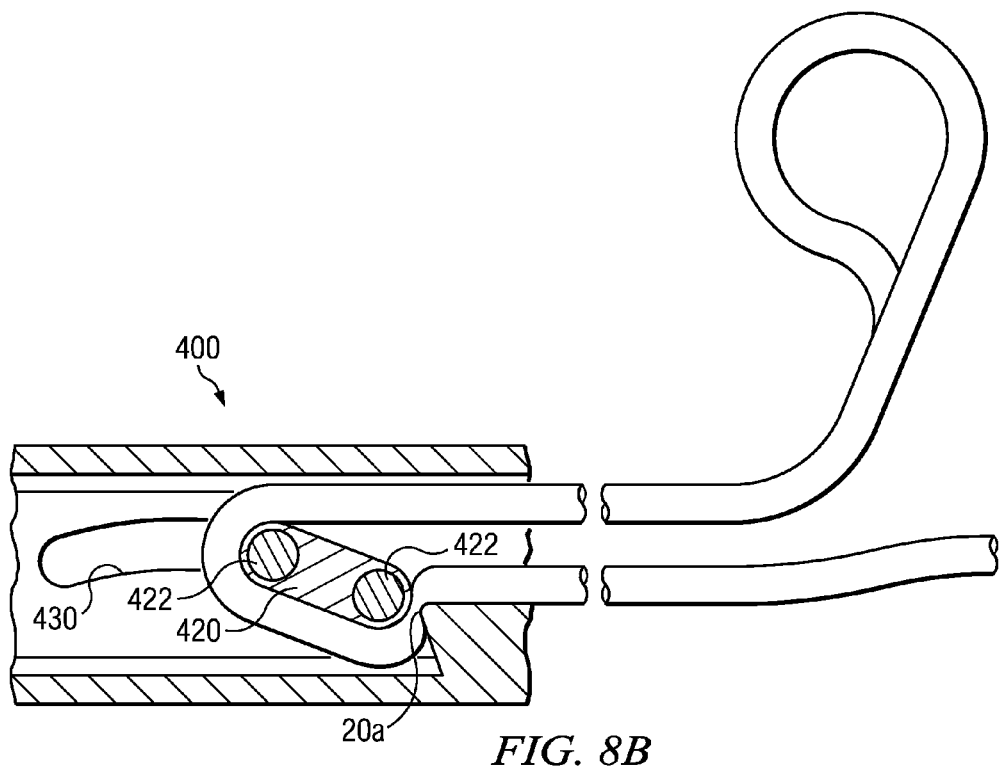

FIGS. 8A and 8B show another suture anchor 400. Suture anchor 400 is similar to that shown in FIGS. 7A and 7B except that the suture locking wedge 420 includes two pins 422 that cooperate with slot 430 to guide the suture locking wedge along a path to the suture locking position shown in FIG. 8B.

Although two pins or projections are shown in the embodiment shown in FIGS. 8A and 8B, the number of pins or protrusion may vary. Indeed a wide variety of connecting means may be utilized to facilitate the movement along a restricted path of the suture locking wedge to compress the suture. Preferably, the connecting means and slots cooperate to allow movement of the suture locking wedge in both a translational and an angular direction (e.g., an arcuate path). When tension on the suture leg 28a arises, the suture locking wedge is moved and leveraged to put an increased compression force on the suture 28.

Methods for Tissue Repair

Figure 9:
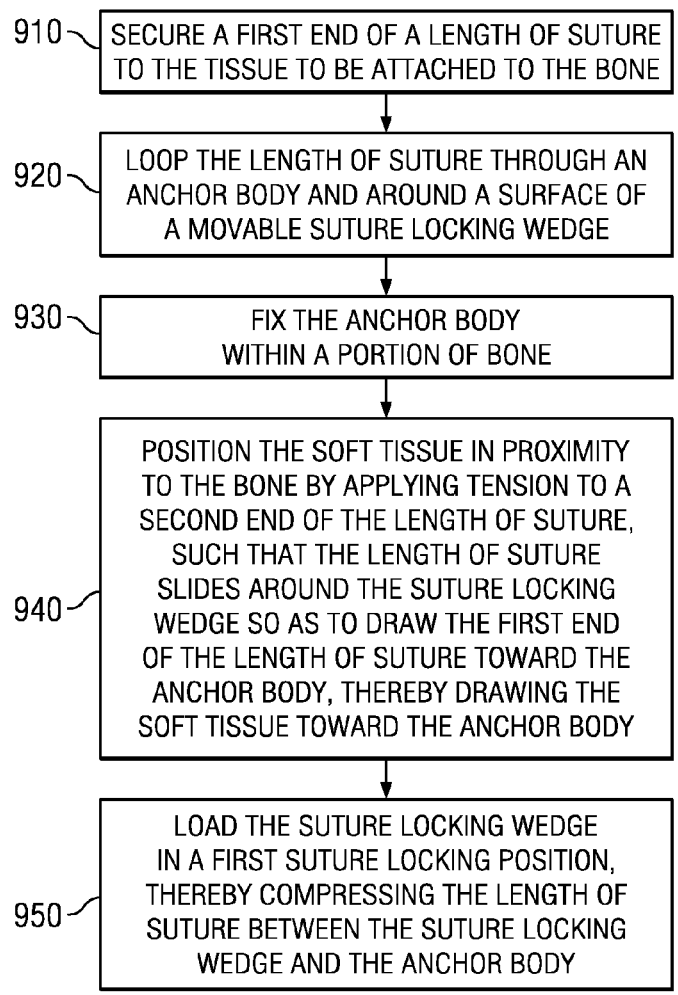
FIG. 9 shows a flow diagram of a method to secure connective tissue to bone.

FIG. 9 is a flowchart showing the steps of a medical procedure for securing connective tissue to bone. This procedure includes the steps of securing a first end of a length of suture to a portion of connective tissue to be attached to a portion of bone, using any method deemed suitable to the clinician (Step 910).

Step 920 states to loop the length of suture through a lumen in a body of a suture anchor device and about a suture locking wedge disposed along the length of the lumen.

The suture anchor device may be temporarily attached to an insertion instrument shaft distal end, having an opening to provide a passage for the length of suture to gain access to the suture anchor device as described in previous embodiments. The shaft distal end may also have a driver to deploy an anchoring element, disposed at the proximal end of the anchoring device.

Next, the suture anchor is inserted into a portion of bone, deep enough so that the anchor device proximal end is in the cancellous bone region. A marker or indicator may be present on the shaft distal end to aid in proper anchor placement. And to deploy or fix the anchoring portion or anchoring element to secure the suture anchor device in surrounding bone (930).

Step 940 states to apply tension to the second end of the length of suture, such that the length of suture slides around the suture locking wedge, so as to draw the first end of the length of suture toward the suture anchor device, thereby drawing the connective tissue closer to the anchor. The second end of the suture is drawn until the portion of connective tissue is snugly secured to the portion of bone.

Step 950 states to guide the suture locking wedge along a path to a first suture locking position, thereby compressing the suture at a first contact location between the suture locking wedge and the anchor body. The path preferably comprises an angular dimension and a translational dimension. This step may be carried out by modifying the tension on the second limb (e.g., pausing, adjusting, or releasing tension on the free limb) so as to allow the tension on the tissue bound end to move the suture locking wedge.

Should the connective tissue need to be relocated, tension may be increased to the second length of suture (the free side), sufficient enough to move the suture locking wedge so as to increase the gap and allow the length of suture to slide around the suture locking wedge, such that the soft tissue may be re-positioned relative to the portion of bone. After the connective tissue has been relocated, the tension may then be increased to the first end of the length of suture again, so as to compress the suture again. The insertion instrument may then be removed from the area.

In another embodiment the method further comprises repeating steps 940 and 950 to reposition the soft tissue and to re-tension the suture. Additionally, applying tension may be performed by pulling on the second end of the suture by hand or otherwise.

Figure 10:
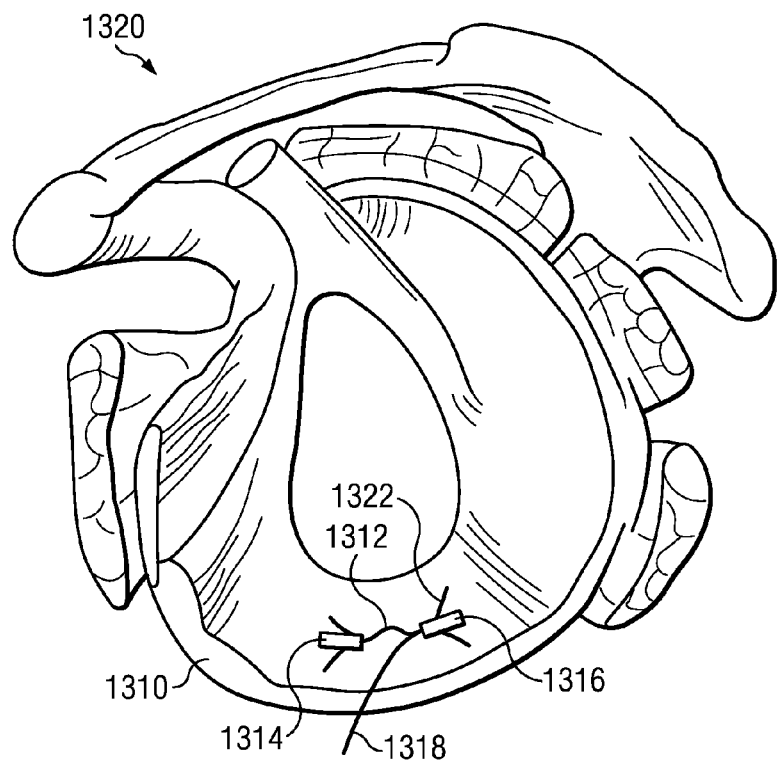
FIG. 10 is an illustration of a method for repairing a capsular tissue.

FIG. 10 illustrates a method for repairing capsular tissue. As shown, a glenoid section 1320 of a shoulder joint includes capsular tissue 1310. The capsular tissue 1310 serves to hold the humeral head in the shoulder joint. It should not be loose. However, if the capsular tissue is stretched (e.g., due to injury) the shoulder becomes loose. This is undesirable.

Repairing the capsule may be performed by stitching folds in the capsule to shrink its effective size (namely, plication). Tightening the capsule to the proper degree makes the shoulder more stable. Folds may be stitched in various manners. In one embodiment, and with reference to FIG. 10, a method comprises securing a first limb of a suture 1312 to a first anchor 1314.

A second limb of the suture 1312 is threaded or looped through a second anchor 1316. The anchors may have features similar to the anchors described herein. In the anchors shown in FIG. 10, radially deflectable members 1322 fix the anchor to the tissue.

Next, the first anchor 1314 and second anchor 1316 are placed in the tissue 1310 and connected with suture 1312.

FIG. 10 shows the anchors separated by a region. Suture 1312 can be tightened incrementally by pulling on free suture limb or tail 1318. The amount of tension applied to the suture 1312 decreases the size of the region, tightening the capsule tissue 1310. This affects the stability and range of motion in the joint. The method thus allows the surgeon to increase tensions until a suitable stabilization is achieved that does not affect range of motion.

Figure 11:
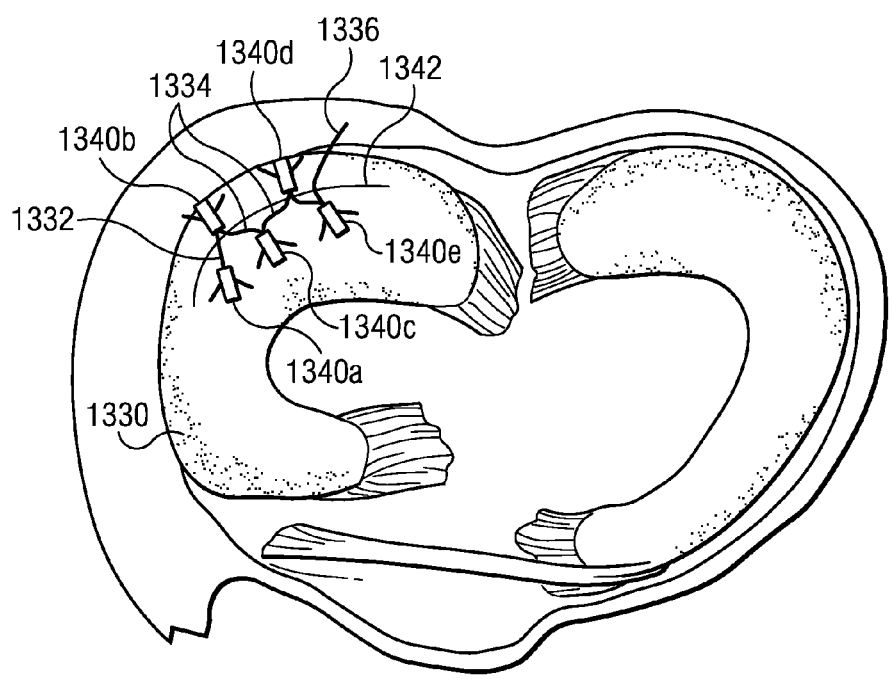
FIG. 11 is an illustration of a method for repairing a meniscus.

FIG. 11 illustrates another method for repairing soft tissue and in particular, a method for repairing a radial tear 1342 in the lateral meniscus 1330 of a knee.

Initially, the method comprises securing a first limb 1332 of a length of suture to a first anchor 1340a.

Next, the suture is looped or threaded through additional anchors 1340b, 1340c, 1340d, and 1340e such that a free suture limb 1336 extends from the last-threaded anchor. In the embodiment shown in FIG. 11, anchor 1340e is the last anchor of the sequence and free suture limb 1336 is shown extending therefrom. Although five anchors are shown in FIG. 11, the number may vary. In a preferred embodiment, the number of anchors placed ranges from 2-10. Generally, fewer anchors would preferably, but not necessarily, be deployed to close a smaller tear. More anchors (e.g., 6 or more) would preferably, but not necessarily, be deployed to close a larger tear.

Next, anchors 1340a, b, c, d, e are placed, one at a time, in the tissue such that the suture length extending between any two anchor bodies spans the tear. For example, anchor 1340b is next or adjacent in sequence to 1340a and the suture portion 1332 between the anchors 1340a and 1340b is shown spanning tear 1342.

Next, the physician pulls on the free suture limb 1336. This step places tension on the suture spanning the tear 1342, closing the tear so that it may heal.

Other modifications and variations can be made to the disclosed embodiments without departing from the subject invention. For example, other methods for anchor deployment will be apparent to the skilled artisan. Moreover, the instruments and methods described herein may be utilized in other regions of the body (e.g., knee, hip, etc.) and for other tissue treatment procedures. Thus, while the exemplary embodiments have been described in detail, by way of example and for clarity of understanding, a variety of changes, adaptations, and modifications will be obvious to those of skill in the art. Therefore, the scope of the present invention is limited solely by the appended claims.

What is claimed is:

1. An anchor device for repairing soft tissue with a suture, the anchor device comprising:
    an anchor body comprising a wall, and the wall defining a lumen;
    a suture locking wedge movably disposed at least partially within the lumen
    a suture being in contact with the suture locking wedge, wherein the suture extends-through the anchor device and loops around the suture locking wedge; and
    wherein the anchor body further comprises a wedge guide comprising at least one elongate arcuate shaped slot formed in the wall of the anchor body, wherein the elongate arcuate shaped slot engages a portion of the suture locking wedge so as to restrict movement of the suture locking wedge to a path such that when a tension force is applied to a first limb of the suture, the suture locking wedge is urged into a first position in which the suture is compressed between the suture locking wedge and a first contact location of the anchor body and wherein the path has a length that comprises an angular dimension and a translational dimension with respect to a longitudinal axis of the anchor body.

2. The anchor device of claim 1 wherein said elongate arcuate shaped slot has a length in the range of 2 to 10 mm.

3. The anchor device of claim 1 wherein said elongate arcuate shaped slot has a constant height.

4. The anchor device of claim 1 wherein said suture locking wedge comprises two opposing substantially planar surfaces that form an angle with an anchor body longitudinal axis when in the first position.

5. The anchor device of claim 1 wherein said suture locking wedge is curved.

6. The anchor device of claim 1 wherein said elongate arcuate shaped slot comprises a recess formed in the wall of the anchor body.

7. The anchor device of claim 1 wherein said guide comprises a protrusion from the wall of the anchor body, and the suture locking wedge comprises a recess which is sized to engage and track the protrusion.

8. The anchor device of claim 1 wherein said anchor body further comprises a bone fixation structure for securing the anchor device in the bone wherein the bone fixation structure is selected from the group consisting of threads, ridges, barbs, and wings.

9. The anchor device of claim 1 wherein at least one of the anchor body and the suture locking wedge comprises an elastic section which deforms when the suture locking wedge is placed in the first position.

10. The anchor device of claim 1 wherein said first contact location comprises a surface parallel to the longitudinal axis of the anchor body.

11. The anchor device of claim 1 wherein said first contact location comprises a surface not parallel to the longitudinal axis of the anchor body.

12. The anchor device of claim 1 wherein said translational dimension and angular dimension guides the suture locking wedge into complementary engagement with the first contact location when the tension force on the first limb is applied.

13. The anchor device of claim 1 wherein said path is shaped such that when a second tension force is applied to a second limb of the suture the suture locking wedge is urged away from the first contact location such that the suture is not compressed.

14. An anchor device for attaching soft tissue to bone with a suture, the anchor device comprising:
    a suture locking wedge movably disposed at least partially within the anchor device and being in contact with the suture when the suture extends through the anchor device and loops around the suture locking wedge; and
    an elongate arcuate shaped wedge track formed in a portion of a wall of the anchor device engaging with and guiding the suture locking wedge along a path to a first position when a tension force is applied to a first limb of the suture in which the suture is compressed between the suture locking wedge and a first contact location of the anchor device and wherein the path is defined by a length of the elongate arcuate shaped wedge track having a portion which forms an angle with a longitudinal axis of the anchor.

15. The anchor device of claim 14 wherein the elongate arcuate shaped wedge track comprises at least two slots in the wall of the anchor body and the suture locking wedge has a portion which engages the slots.

16. The anchor device of claim 15 wherein said suture locking wedge is substantially planar.

17. The anchor device of claim 15 wherein said at least two slots each have a length in the range of 2 to 10 mm.

18. The anchor device of claim 14 wherein said elongate arcuate shaped wedge track comprises a translational dimension and an angular dimension with respect to the anchor longitudinal axis.

19. The anchor device of claim 14 wherein said elongate arcuate shaped wedge track comprises a recess in the wall of the anchor body.

20. The anchor device of claim 14 wherein said elongate arcuate shaped wedge track comprises a protrusion from the wall of the anchor body, and the suture locking wedge comprises a recess sized to engage the protrusion.

21. The anchor device of claim 14 further comprising a bone fixation structure for securing the anchor device in the bone wherein the bone fixation structure is selected from the group consisting of threads, ridges, barbs, and wings.

22. The anchor device of claim 14 wherein at least one of the anchor body and the suture locking wedge comprises an elastic section which deforms when the suture locking wedge is placed in the first position.

23. The anchor device of claim 14 wherein the elongate arcuate shaped wedge track guides the suture locking wedge away from the first contact location when a second tension force is applied to a second limb of the suture such that the suture is not compressed.

24. The anchor device of claim 14 wherein said angle ranges between 10 and 50 degrees.

25. A method for securing soft tissue to bone comprising:
(a) securing a first limb of a length of suture to the soft tissue to be attached to the bone;
(b) extending the length of suture through an anchor body and around a surface of a suture locking wedge movably disposed at least partially within the anchor body;
(c) fixing the anchor body within the bone;
(d) approximating the soft tissue in proximity to the anchor body by applying a first tension to a second limb of the length of suture, such that the length of suture slides around the suture locking wedge so as to draw the soft tissue toward the anchor body; and
(e) moving the suture locking wedge along a wedge path defined in the anchor body such that the suture locking wedge moves to a first suture locking position, compressing the length of suture between the suture locking wedge and the anchor body, and wherein the moving comprises moving the suture locking wedge along the wedge path, the wedge path defined by a slot formed in the anchor body that engages the suture locking wedge and wherein the slot has an elongate arcuate shape.

26. The method of claim 25 wherein the approximating step is carried out until the soft tissue is moved within a threshold distance from the anchor body, such that a second tension arises on a first limb from the soft tissue.

27. The method of claim 26 wherein the step of moving the suture locking wedge is carried out by halting applying the first tension on the second limb, thereby causing the second tension on the first limb of the suture to move the suture locking wedge along the wedge path.

28. The method of claim 27 further comprising repeating steps (d) and (e) to reposition the soft tissue and to re-tension and lock the suture.

29. The method of claim 27 wherein the second tension is increased by pulling on the first limb of the suture by hand.

30. The method of claim 26 wherein the threshold distance is between 3 and 6 mm.

31. The method of claim 26 further comprising the step of applying a third tension on the second limb of the suture to unseat the suture locking wedge subsequent to said step (e) to release the suture from being compressed.

32. The method of claim 25 wherein the angle angular dimension comprises a linear direction at an angle (a) to a longitudinal axis of anchor body wherein the angle ($\alpha$) ranges from 10 to 50 degrees.

33. The method of claim 32 wherein the extending step comprises looping the length of suture through the anchor body and around the surface of the suture locking wedge.

34. A method for securing soft tissue to bone comprising:
(a) securing a first limb of a length of suture to the soft tissue to be attached to the bone;
(b) extending the length of suture through an anchor body and around a surface of a suture locking wedge movably disposed at least partially within the anchor body;
(c) fixing the anchor body within the bone;
(d) approximating the soft tissue in proximity to the anchor body by applying a first tension to a second limb of the length of suture, such that the length of suture slides around the suture locking wedge so as to draw the soft tissue toward the anchor body until the soft tissue is moved within a threshold distance from the anchor body, such that a second tension arises on the first limb from the soft tissue;
(e) halting applying the first tension on the second limb, causing the second tension on the first limb to move the suture locking wedge along a wedge path defined in the anchor body such that the suture locking wedge moves to a first suture locking position, compressing the length of suture between the suture locking wedge and the anchor body, and wherein the moving comprises moving the suture locking wedge in a direction comprising an angular dimension and a translational dimension;
(f) increasing the second tension on the first limb by pulling on the first limb by hand; and
(g) repeating steps (d) and (f) to reposition the soft tissue and to re-tension and lock the suture.

\* \* \* \* \*